United States Patent
Rougeot et al.

(10) Patent No.: US 7,153,833 B2
(45) Date of Patent: Dec. 26, 2006

(54) THERAPEUTIC USES OF SMR1 PEPTIDES

(75) Inventors: Catherine Rougeot, Chevreuse (FR); François Rougeon, Sevres (FR)

(73) Assignees: Institut Pasteur, Paris (FR); Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 10/451,064

(22) PCT Filed: Dec. 24, 2001

(86) PCT No.: PCT/IB01/02819

§ 371 (c)(1),
(2), (4) Date: Dec. 1, 2003

(87) PCT Pub. No.: WO02/051435

PCT Pub. Date: Jul. 4, 2002

(65) Prior Publication Data

US 2004/0116342 A1    Jun. 17, 2004

(30) Foreign Application Priority Data

Dec. 22, 2000 (EP) ................................. 00403670

(51) Int. Cl.
| | |
|---|---|
| A61K 38/22 | (2006.01) |
| A61P 25/00 | (2006.01) |
| A61P 29/00 | (2006.01) |
| A61G 27/00 | (2006.01) |
| C07L 14/575 | (2006.01) |
| G01N 33/50 | (2006.01) |

(52) U.S. Cl. .............................. 514/15; 514/2; 514/16; 514/17

(58) Field of Classification Search ...................... None
See application file for complete search history.

(56) References Cited

U.S. PATENT DOCUMENTS

| | | | | |
|---|---|---|---|---|
| 5,302,582 | A | * | 4/1994 | Vertesy et al. ................. 514/23 |
| 5,550,119 | A | * | 8/1996 | De Lombaert et al. ....... 514/92 |
| 5,859,189 | A | | 1/1999 | Rosinski-Chupin et al. 530/330 |
| 6,025,143 | A | | 2/2000 | Rosinski-Chupin et al. ......................... 435/69.1 |
| 6,589,750 | B1 | | 7/2003 | Rougeot et al. ............ 435/7.21 |
| 6,818,405 | B1 | | 11/2004 | Rougeot et al. .............. 435/7.1 |
| 2003/0078200 | A1 | | 4/2003 | Marcel et al. ................. 514/12 |
| 2003/0170620 | A1 | | 9/2003 | Rosinski-Chupin et al. ... 435/6 |
| 2003/0186870 | A1 | | 10/2003 | Marcel et al. ................. 514/12 |
| 2003/0195155 | A1 | | 10/2003 | Rougeot et al. .............. 514/12 |

FOREIGN PATENT DOCUMENTS

| | | |
|---|---|---|
| JP | 2980334 | 11/1999 |
| WO | 90 03981 | 4/1990 |
| WO | WO 90/03981 | 4/1990 |
| WO | 98 37100 | 8/1998 |

OTHER PUBLICATIONS

Catherine Rougeot et al.: "Rodent submandibular gland peptide hormones and other biologically active peptides" PEPTIDES, vol. 21, No. 3, pp. 443-455, 2000.

* cited by examiner

*Primary Examiner*—Jeffrey Edwin Russel
(74) *Attorney, Agent, or Firm*—Oblon, Spivak, McClelland, Maier & Neustadt, P.C.

(57) ABSTRACT

A method for treating or reducing the severity of a disease or disorder mediated by a membrane metallopeptidase by administering to a mammal a SMR1-peptide or a pharmaceutically active amount of a SMR1-peptide.

35 Claims, 9 Drawing Sheets

THERAPEUTIC USES OF SMR1 PEPTIDES

In a first aspect, the invention relates to new therapeutic uses of a SMR1-peptide.

The inventors have previously characterized a new rat submandibular gland protein, named SMR1 (submandibular rat 1 protein), which has the structure of a prohormone and whose synthesis is under androgen control (Rosinsky-Chupin et al., (1988), *Proc. Natl. Acad. Sci. USA;* 85(22): 8553–7) and PCT Patent Application No. WO 90/03981). The gene encoding SMR1 belongs to a new multigene family, the VCS family, which has been localized to rat chromosome 14, bands p21–p22 (Courty et al., (1996) *Mol. Biol. Evol.* 13(6):758–66; Rosinsky-Chupin et al., (1995) *Mamm. Genome* 6(2): 153–4)) and for which some human gene members have been characterized (Isemura et al., (1997), *J Biochem* 121:1025–1030; Isemura et al. (1994) *J Biochem* 115:1101–1106; Isemura et al. (1979) *J Biochem* 86:79–86; Dickinson et al. (1996) *Curr Eye Res* 15:377–386). The gene has an organization similar to a number of hormone precursor genes (Rosinsky-Chupin et al., (1990) *DNA Cell. Biol.* 9(8):553–9). SMR1 mRNA is expressed in a highly tissue-, age- and sex-specific manner in the acinar cells of the male rat submaxillary gland (SMG) and in the prostate (Rosinsky-Chupin et al., (1993) *Histochem. Cytochem.* 41(11):1645–9).

It has been described that, in vivo, SMR1 is selectively processed at pairs of basic amino acid sites in a tissue- and sex-specific manner to give rise to mature peptide products, in a manner similar to the maturation pathway of peptide-hormone precursors (Rougeot et al., (1994) *Eur. J. Biochem.* 219(3):765–73). The structurally related peptides generated from SMR1 by cleavage at pairs of arginine residues (e.g. the undecapeptide: VRGPRRQHNPR (SEQ ID NO: 4); the hexapeptide: RQHNPR (SEQ ID NO: 9); and the pentapeptide: QHNPR (SEQ ID NO: 2)) are in vivo selectively matured from the precursor after processing at pairs of basic amino acid residues by a paired basic amino acid-converting enzyme, likely the Furine convertase,—differentially accumulated in a tissue-, age- and sex-related manner, and—locally as well as systemically released upon multifactorial neuroendocrine control (Rougeot et al, 1994).

In such a context, the final mature peptide generated from SMR1, named SMR1-Pentapeptide (SMR1-QHNPR (SEQ ID NO: 2)), also named sialorphin, is synthesized predominantly in response to androgen steroids and is constitutively released into the bloodstream in basal condition and acutely released in response to environmental stress, depending on the state of activation of adrenoreceptors controlling the secretory responsiveness of the SMG.

In turn, the circulating SMR1-Pentapeptide is in vivo rapidly and selectively taken up by peripheral targets through specific binding sites, predominantly within renal, bone and dental tissues.

The fact that the target sites of the peptide are mainly localized within the major tissues of ion capture, transport and regulation, gives evidence that SMR1-Pentapeptide might play a local and systemic role in modulating mineral ion homeostatic process, in vivo. Furthermore, associated with the fact that the androgen-regulated SMR1-Pentapeptide is upon environmental stress acutely secreted, these findings led the inventors to postulate that this SMG-specific signaling peptide might participate in mediating integrative reestablishment of dynamic homeostatic responses: to stressful situations within male rat-specific behavioral characteristics such as aggressive and/or sexual intercourses, and in relation to female-specific physiological characteristics such as pregnancy and lactation.

WO 98/37 100 discloses that the maturation products of the SMR1 protein, specifically the peptide of structural formula XQHNPR (SEQ ID NO: 10), recognize specific target sites in organs that are deeply involved in the mineral ion concentration. This discovery has led the inventors to assign to the SMR1-peptide (especially the SMR1-pentapeptide, hexapeptide or undecapeptide) an active role in the regulation of the metal ion concentrations in the body fluids and tissues, and thus a therapeutic role of these peptides in all the metabolic disorders related to a mineral ion imbalance.

Namely, the therapeutic peptides disclosed therein are useful for treating or preventing bone, teeth, kidney, intestine, pancreas, stomach, or salivary gland disorders caused by a mineral ion imbalance in the body fluids or tissues, namely hyper- or hypo-parathyroidism, osteoporosis, pancreatitis, submandibular gland lithiasis, nephrolithiasis or osteodystrophy.

On the basis of the hypothesis mentioned above, a behavioral pharmacological approach has been undertaken. SMR1-peptide, especially SMR1-Pentapeptide was found to induce a dose-dependent improvement on the sexual behavior of adult male rats with a loss of the aggressive impulse behavior seen in control rats (PCT patent application WO 01/00 221).

To elucidate the pathways that have taken place in the SMR1-peptide action, one of the essential steps was to investigate the molecular characteristics of the peptide-receptor sites. The isolation of the membrane binding site accessible to the systemic administration or radiolabelled SMR1-Pentapeptide, especially within the renal outer medulla has been achieved. The identification of its amino-acid sequence has revealed that the cell surface molecule which binds the peptide in vivo, is a membrane metallopeptidase and more specifically a mammalian type II integral membrane zinc-containing endopeptidase, i.e. Neutral EndoPeptidase 24-11 or NEP, also named Enkephalinase that belongs to the Neprilysin subfamily, which plays critical role in the functional potency of various peptidergic signals. Moreover, the in vivo direct interaction of rat kidney NEP and SMR1-Pentapeptide was demonstrated in vitro using purified rabbit kidney NEP.

Furthermore, at the level of whole rat body a good (topological and kinetical) correspondence was found in vivo between the distribution of target organs accessible to circulating radiolabelled SMR1-Pentapeptide and that of known synthetic NEP inhibitor (3HHACBO-Gly) (Sales et al, (1991) *Regulatory Peptides* 33, 209–22). Otherwise, a number of observations argue for the hypothesis that SMR1-peptide is a SMG-derived natural modulator, especially an inhibitor, of the NEP activity:

1—the SMR1-Pentapeptide tissue uptake was found to be pharmacokinetically and biochemically stable in vivo, 2—the SMR1-peptide does not share the residues required to be a NEP substrate, seeing that the NEP preferentially cleaves peptides between the X-Phe bond, and 3—the SMR1-Pentapeptide has strong zinc-chelating group, which has been designed for the potent synthetic NEP inhibitors.

In view of the numerous physiological NEP substrates (namely the peptide hormones: Enkephalins, Substance P, Bradykinin, Angiotensin II and atrial natriuretic peptide), physiological consequences of the NEP/SRM1-peptide interaction are expected to impact on the control of central and peripheral pain perception, inflammatory phenomena, arterial tone and/or mineral exchange (Roques et al, 1993 infra).

Neutral endopeptidase, NEP 24-11, is distributed both in nervous and peripheral tissues of mammals, and in the periphery it is particularly abundant in the kidney and placenta. In these tissues the cell-surface metallopeptidase NEP participates in the postsecretory processing and metabolism of neuropeptides, systemic immunoregulatory peptides and peptide-hormones. By controlling the active levels of circulating or secreted regulatory peptides, NEP modulates their physiological receptor-mediated action. Hence, the membrane-anchored NEP is involved in regulating the activity of: potent vasoactive peptides such as Substance P, Bradykinin (BK), Atrial Natriuretic peptide (ANP), and Angiotensin II (AII); potent inflammatory/immunoregulatory peptides such as Substance P and BK and fMet-Leu-Phe (fMLP); potent opioid neuropeptides such as Met and Leu-Enkephalins (Enk) and potent mineral exchange and fluid homeostasis regulatory peptides such as ANP, C-type Natriuretic Peptide (CNP) and B-type Natriuretic Peptide (BNP). However the levels of these peptides are changed through the NEP-induced formation/degradation only in regions where they are tonically released or where their release is triggered by a stimulus.

From an integrative point of view, the NEP biological activity is to control the active levels of peptidergic signals involved in arterial tension regulation, in inflammatory phenomena and in water-mineral homeostasis, as well as, in the control of pain processing. From a clinical point of view, this substantiates the fact that NEP is an important drug target in various disease states. For example, by inhibiting NEP, thereby increasing the levels and duration of action of central or peripheral endogenous opioids, an analgesic or antidiarrheal agent could be obtained, or by inhibiting endogenous AII formation and substance P, BK and ANP inactivation, antihypertensive, natriuretic and diuretic agents could be obtained. The main advantage of modifying the concentrations of endogenous peptides by use of NEP inhibitors is that the pharmacological effects are induced only at receptor stimulated by the natural effectors, and are critically dependent on the tonic or stimulus-evoked release of the natural effectors happening upon environmental, behavioral and physiopathological stressful situations (Roques et al, (1993) *Pharmacological Reviews* 45, 87–146). It is important to stress that in such stressful context, the natural potential NEP-modulator, SMR1-peptide, will be also acutely and tonically released, distributed and taken up by its systemic target tissues, especially by the renal NEP sites (Rougeot et al, 1997). Thereby, the SMR1-peptide would be in vivo kinetically bioavailable to modulate NEP activity and so to optimize the local and systemic inflammatory, pressor and/or ion homeostatic responses to stress. The integrative point of view is in concordance with the assumption that circulating Submaxillary Gland (SMG)-derived factors might participate in integrative reestablishment of homeostatic responses to physiological or pathological "stress states" (injury, trauma or infection), rather than contribute to the resting homeostatic steady state (Rougeot et al, (2000) *Peptides* 21, 443–55).

From a general point of view, evidence of a physiological significance demonstrates the existence of a Cervical Sympathetic Trunk (CST)-SMG neuroendocrine axis that plays an integral role in physiological adaptations and contributes to the maintenance of homeostasis in mammals, especially under the "stress conditions" seen in rodents with tissue damage, inflammation, and aggressive behavior. The data gathered in the laboratory provide convincing evidence that SMR1-peptide is a novel signaling mediator, adapted to the sex, and species-specific environmental, behavioral and physiological characteristics, tonically and dynamically mobilized upon urgent situations, in the way to optimize both local and systemic nociceptive, inflammatory, pressor and/or ion homeostatic responses, through regulation of the membrane-bound NEP activity. Otherwise, the SMR1-peptide, which is to date the first natural regulator of the peripheral NEP activity identified, seems to be designed as a new class of therapeutic molecules as this metallopeptidase is well-conserved especially between rat, rabbit and human species with sequence homology $\geq 90\%$.

The evidence provided by the inventors together with the striking homology with the NEP sequences between species further suggest that the SMR1-peptide may act as natural modulator/inhibitor of membrane metallopeptidases, notably zinc metallopeptidases (GenBank Access number P 08473, Malfroy et al, (1988) FEBS Lett. 229(1), 206–210; NP 258428, Bonvouloir et al, (2001) DNA Cell Biol. 20(8), 493–498; NP 036740, Malfroy et al. (1987) Biochem Biophys Res Commun 144, 59–66).

Examples of mammalian membrane metallopeptidases besides NEP are ECE (Endothelin-Converting Enzymes), in particular ECE1 and ECE2, the erythrocyte cell-surface antigen KELL and the product of PEX gene associated with X-linked hypophosphatemic rickets, as well as ACE (Angiotensin Converting Enzyme) and APN (Aminopeptidase N).

Inhibition of ACE and/or ECE has a significant application in the treatment of hypertension and the prevention and treatment of atherosclerosis.

Inhibition of APN in conjunction with NEP has significant application in the treatment of pain.

Inhibition of related membrane metallopeptidases has therapeutic effects in the treatment of tumors, namely ovarian, colorectal, brain, lung, pancreas, gastric and melanoma cancers, and reducing the incidence of metastasis, atherosclerosis and/or hypertension. Inhibitions of related membrane metallopeptidases has also therapeutic effects in pain controlling. Such antinociceptive effects on acute pain are analgesic effects but also effects on chronic inflammatory pain such as arthritis or inflammatory bowel disease.

Furthermore, inhibition of bacterial or viral metallopeptidase is expected to have anti-infection effects.

Metallopeptidases playing an important role in pathogen host tissue invasion and immunological and inflammatory processes, for example those of *Streptococcus pyogenes, Pseudomonas aeruginosa, Porphyromonas gingivalis* and *Legionella pneumophila*.

Furthermore, bacterial metallopeptidases, especially zinc-metallopeptidases play an important role in the diseases caused by proteolytic toxins, such as the toxins of *B. anthracis* (Anthrax Lethal factor) and the neurotoxins of *C. tetanum* and *botulinum*.

Other metallopeptidases play an important role in various infections such as infections caused by HIV (FR 2 707 169).

The importance of proteinase inhibitors for the treatment of bacterial or viral diseases may be found in J. Potempa, J. Travis, (Proteinases as virulence factors in bacterial diseases and as potential targets for therapeutic interaction with proteinase inhibitors. In proteases as targets for therapy. 99, 159–188—Eds K. Helm, B. D. Korant and J. C. Cheronis—Spinger Handbook Exp. Pharm. 140).

The different roles of metallopeptidases are disclosed in Turner et al, (2001) Bioessays, 23, 261–9; Kenny et al, (1977) Proteinases in mammalian cells and tissues); Kenny et al, (1987) Mammalian ectoenzymes; Beaumont et al, (1996) zinc metallopeptidases in health and disease, 105–129).

A first subject-matter of the invention is thus the therapeutic use of a SMR1-peptide or a pharmaceutically active amount of said SMR1-peptide, for the preparation of a therapeutic composition for preventing or treating diseases wherein a modulation of the activity of a membrane metallopeptidase, notably a membrane zinc metallopeptidase, is sought, in a mammal, specifically in a human.

Another object matter of the invention is the therapeutic use of an agent such as a biologically active derivative of SMR1-peptide for modulating the interaction between the endogenous SMR1-peptide and said membrane metallopeptidase. Said modulation is a kinetical and/or molecular one.

"Endogenous" refers to a molecule (herein a SMR1-peptide) that is naturally expressed or matured in tissues of a patient to be treated.

The invention further relates to the use of an agent that modulates the interaction between endogenous SMR1 protein or peptide and a membrane metallopeptidase for the preparation of a therapeutic composition for preventing or treating diseases wherein a modulation of the activity of said membrane metallopeptidase is sought.

The present invention concerns more specifically the therapeutic use of the SMR1-peptide or a pharmaceutically active amount of a SMR1-peptide, for the preparation of a medicament for preventing or treating diseases wherein modulation of NEP-induced degradation of NEP-sensitive peptides is sought, in a mammal, specifically in human.

As used in the present specification, SMR1-peptide means the SMR1 protein, a peptide generated from SMR1, also called a maturation product of the SMR1 protein, or one of the biologically active derivatives of said protein or said maturation product.

In a preferred embodiment, the SMR1-peptide is a compound of structural formula (1):

$X_1QHX_2X_3X_4$ (SEQ ID NO: 11)

wherein $X_1$ denotes a hydrogen atom or $X_1$ represents an amino acid chain selected from the following: $X_1$=R or G, $X_1$=RR, or $X_1$=PRR, or $X_1$=GPRR, or $X_1$=RGPRR, or $X_1$=VRGPRR, $X_2$ denotes N, G or D, $X_3$ denotes P or L and $X_4$ denotes R or T.

Preferred peptides comprise peptides of sequence:
QHNPR (SEQ ID NO: 2), RQHNPR (SEQ ID NO: 9) and VRGPRRQHNPR (SEQ ID NO: 4) from *Ratus norvegius*,
QHNLR (SEQ ID NO: 5) and RQHNLR (SEQ ID NO: 6) from *Ratus ratus*,
GQHGPR (SEQ ID NO: 7) and GQHDPT (SEQ ID NO: 8) from mouse.

In the above amino acid sequences:
Q represents Glutamine,
H represents Histidine,
N represents Asparagine,
G represents Glycine,
P represents Proline,
R represents Arginine,
L represents Leucine,
T represents Threonine,
D represents Aspartic acid, and
V represents valine.

"Biologically active derivatives" of the SMR1-peptide refer to function-conservative variants, homologous proteins and peptidomimetics, as well as a hormone, an antibody or a synthetic compound, (i.e. either a peptidic or non peptidic molecule) that preferably retain the binding specificity and/ or physiological activity of the parent peptide, as defined below. They preferably show an ability to bind a membrane metallopeptidase, more particularly NEP. Such binding activity may be readily determined by binding assays, e.g. by labeling the SMR1 derivative or by competition assay with a conventional NEP substrate, optionally labeled.

"Function-conservative variants" are those in which a given amino acid residue in a protein has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine and lysine are hydrophilic-basic amino acids and may be interchangeable. Similarly, isoleucine, a hydrophobic amino acid, may be replaced with leucine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

"Allelic variants" are more particularly encompassed, as described in greater details below.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a particular embodiment, two amino acid sequences are "substantially homologous" or "substantially similar" when greater than 80% of the amino acids are identical, or greater than about 90% are similar and functionally identical. Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

Natural NEP substrates are mainly the peptide hormones: Enkephalins, Substance P, Bradykinin, Angiotensin II and Atrial Natriuretic Peptide which play key role in the control of central and peripheral pain perception, inflammatory phenomena, mineral exchange and/or arterial tone.

More particularly, one object of the present invention is the use of the above described therapeutic peptides as analgesic agents by inhibiting NEP at peripheral, spinal and/or supraspinal levels and thereby increasing the levels and duration of action of central or peripheral endogenous opioids, including enkephalins.

Another object is the use of the above described peptides as antidiarrheal agents.

Another object is the use of the above described peptides as antihypertensive, natriuretic and diuretic agents by inhibiting endogenous AII formation and substance P, BK and ANP inactivation.

A further object is the use of the above described peptides as an agent for preventing or treating atherosclerosis.

Another object is the use of the above described peptides as an agent for the treatment of pain including chronic inflammatory pain, such as arthritis or inflammatory bowel disease.

Another object is the use of the above described peptides as an agent for controlling immuno-inflammatory responses.

Another object is the use of the above described peptides as an agent for preventing or treating the processes of malignant cell proliferation and dissemination.

Another object of the present invention is the use of the above described peptides as a substitute in the treatment of drug abuse, notably morphine drug abuse.

Indeed, studies have suggested that the vulnerability to drug abuse and the development of reward and drug dependence is at least in part, a result of pre-existent or induced modifications and/or defect of the endogenous opioid system. In this regard, using SMR1-peptide to potentiate the effects of endogenous enkephalins will reduce the various side-effects (somatic signs of withdrawal) produced by interruption of chronic morphine or heroin administration.

Still another object of the invention is the use of the above described peptides for treating infections such as bacterial or viral diseases.

For purposes of the invention, the term "mammal" is used in its usual taxonomic sense and specifically includes humans.

For purposes of the invention, a "peptide" is a molecule comprised of a linear array of amino acid residues connected to each other in the linear array by peptide bonds. Such linear array may optionally be cyclic, i.e., the ends of the linear peptide or the side chains of amino acids within the peptide may be joined, e.g., by a chemical bond. Such peptides according to the invention may include from about three to about 500 amino acids, and may further include secondary, tertiary or quaternary structures, as well as intermolecular associations with other peptides or other non-peptide molecules. Such intermolecular associations may be through, without limitation, covalent bonding (e.g., through disulfide linkages), or through chelation, electrostatic interactions, hydrophobic interactions, hydrogen bonding, ion-dipole interactions, dipole—dipole interactions, or any combination of the above.

Preferred peptides according to the invention comprise an amino acid sequence selected from the group consisting of:

| | |
|---|---|
| Glp-His-Asn-Pro-Arg | [SEQ ID NO. 1, where Xaa=Glp] |
| Gln-His-Asn-Pro-Arg | [SEQ ID NO. 2] |
| Arg-Gln-His-Asn-Pro-Arg | [SEQ ID NO. 3] |
| Val-Arg-Gly-Pro-Arg-Arg-Gln-His-Asn-Pro-Arg | [SEQ ID NO 4] |
| Gln-His-Asn-Leu-Arg | [SEQ ID NO 5] |
| Arg-Gln-His-Asn-Leu-Arg | [SEQ ID NO 6] |
| Gly-Gln-His-Gly-Pro-Arg | [SEQ ID NO 7] |
| Gly-Gln-His-Asp-Pro-Thr | [SEQ ID NO 8] | wherein the sequences are shown in N to C configuration, and wherein Glp is pyroglutamate, Gln is glutamine, His is histidine, Asn is asparagine, Pro is proline, Arg is Arginine, Gly is Glycine, Val is Valine, Leu is Leucine, and Thr is Threonine.

In these peptides, by N-terminal cyclization/decyclization, Glp and Gln interconvert.

In addition, certain preferred peptides according to the invention comprise, consist essentially of, or consist of an allelic variant of a peptide shown in any of SEQ ID NO. 1–8. As used herein, an "allelic variant" is a peptide having from one to two amino acid substitutions from a parent peptide, but retaining the binding specificity and/or physiological activity of the parent peptide. As used herein, "retaining the binding specificity of the parent peptide" means being able to bind to a monoclonal or polyclonal antibody that binds to one of the peptides shown in SEQ ID NOS. 1–8 with an affinity that is at least one-tenth, more preferably at least one-half, and most preferably at least as great as that of one of the actual peptides shown in SEQ ID NOS. 1–8. Determination of such affinity is preferably conducted under standard competitive binding immunoassay conditions (Rougeot et al., (E. J. B. 219(3) 765–773). "Retaining the physiological activity of the parent peptide" means retaining the ability of any one of the peptides shown in SEQ ID NOS. 1–8 to bind and to modulate NEP-activity and so to optimize the local and systemic nociceptive, inflammatory, pressor, and/or ion homeostatic responses to stress. Determining whether such activity is modulated is further described later in this specification. The term "allelic variants" is specifically intended to include any human functional homologs of the peptides set forth in SEQ ID NOS. 1–8 which do not have the identical amino acid sequence thereof.

Peptides according to the invention can be conveniently synthesized using art recognized techniques (see e.g., Merifield, J. Am. Chem. Soc. 85: 2149–2154).

Also part of the invention are preferred peptidomimetics retaining the binding specificity and/or physiological activity of the parent peptide, as described above. As used herein, a "peptidomimetic" is an organic molecule that mimics some properties of peptides, preferably their binding specificity and/or physiological activity. Preferred peptidomimetics are obtained by structural modification of peptides according to the invention, preferably using unnatural amino acids, D amino acid instead of L amino acid, conformational restraints, isosteric replacement, cyclization, or other modifications. Other preferred modifications include without limitation, those in which one or more amide bond is replaced by a non-amide bond, and/or one or more amino acid side chain is replaced by a different chemical moiety, or one of more of the N-terminus, the C-terminus or one or more side chain is protected by a protecting group, and/or double bonds and/or cyclization and/or stereospecificity is introduced into the amino acid chain to increase rigidity and/or binding affinity.

Still other preferred modifications include those intended to enhance resistance to enzymatic degradation, improvement in the bioavailability in particular by nervous, intestinal, placental and gonad tissues and more generally in the pharmacokinetic properties and especially comprise:

protecting the $NH_2$ and COOH hydrophilic groups by esterification (COOH) with lipophilic alcohols or by amidation (COOH) and/or by acetylation ($NH_2$) or added carboxyalkyl or aromatic hydrophobic chain at the $NH_2$ terminus;

retroinversion or reduction isomers of the CO—NH amide bonds or methylation (or ketomethylene, methyleneoxy, hydroxyethylene) of the amide functions;

substitution of L amino acids for D amino acids;

dimerisation of amino acid peptide chain.

All of these variations are well known in the art. Thus, given the peptide sequences disclosed herein, those skilled in the art are enabled to design and produce peptidomimetics having binding characteristics similar to or superior to such peptides (see e.g., Horwell et al., Bioorg. Med. Chem. 4: 1573 (1996); Liskamp et al., Recl. Trav. Chim. Pays-Bas 1: 113 (1994); Gante et al., Angew. Chem. Int. Ed. Engl. 33: 1699 (1994); Seebach et al., Helv. Chim. Acta 79: 913 (1996)).

The peptides used according to the present invention may be prepared in a conventional manner by peptide synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups.

For solid phase synthesis, the technique described by Merrifield may be used in particular. Alternatively, the technique described by Houbenweyl in 1974 may also be used.

For more details, reference may be made to WO 98/37 100.

The peptides used in the therapeutic method according to the present invention may also be obtained using genetic engineering methods. The nucleic acid sequence of the cDNA encoding the complete 146 amino acid SMR1 protein has been described in the PCT Patent Application No. WO 90/03891 (Rougeon et al.) For the biologically active peptide derivatives of the SMR1-peptide, for example a derivative of $X_1QHX_2X_3X_4$ (SEQ ID NO: 11), a person skilled in the art will refer to the general literature to determine which appropriate codons may be used to synthesize the desired peptide.

The methods that allow a person skilled in the art to select and purify the biologically active derivatives that bind to the same targets and have an agonist or an antagonist biological activity of the SMR1-peptide of the invention are described hereunder.

The biologically active derivative of the SMR1-peptide may be a protein, a peptide, a hormone, an antibody or a synthetic compound which is either a peptide or a non peptidic molecule, such as any compound that can be synthesized by the conventional methods of organic chemistry.

Selection of the biologically active derivatives of the SMR1-peptide of the invention is performed both in assessing the binding of a candidate ligand molecule to the NEP binding site for the QHNPR (SEQ ID NO: 2) pentapeptide, and in determining the metabolic changes induced by this candidate molecule on its target, such as the synthesis and/or release of the primary or secondary messenger metabolites as a result of a transduction signal via the protein kinases or adenylate cyclase and the activation of a protein of the G family or the variation of the enzymatic activity of NEP, specifically on the metabolism of natural NEP substrates.

Binding assays of the candidate molecule are generally performed at 4° C. to 25° C. or 37° C. In order to facilitate the reading of the hereinafter described protocol, QHNPR (SEQ ID NO: 2) pentapeptide is also used instead of or in competition with a biologically active derivative candidate molecule.

Accordingly, another object of the present invention is a process for screening ligand molecules that specifically bind to the NEP binding site for the QHNPR (SEQ ID NO: 2) pentapeptide, comprising the steps of:

a) preparing a cell culture or preparing an organ specimen or a tissue sample (cryosections or slices or membrane preparations or crude homogenates) containing NEP binding sites for the QHNPR (SEQ ID NO: 2) pentapeptide;

b) adding the candidate molecule to be tested in competition with half-saturating concentration of labeled pentapeptide;

c) incubating the cell culture, organ specimen or tissue sample of step a) in the presence of the candidate molecule during a time sufficient and under conditions for the specific binding to take place;

d) quantifying the label specifically bound to the cell culture, organ specimen or tissue sample in the presence of various concentrations of candidate molecule (preferably $10^{-10}$ to $10^{-5}$ M).

In said above process, a half-saturating concentration is the concentration of the labeled QHNPR (SEQ ID NO: 2) pentapeptide which binds 50% of the NEP binding sites.

This process also allows to define the relative affinity of the candidate molecule compared to the QHNPR (SEQ ID NO: 2) affinity.

Another object of the present invention is a process for determining the relative affinity of ligand molecules that specifically bind to the NEP binding sites for the QHNPR (SEQ ID NO: 2) pentapeptide comprising the steps a), b), c) and d) of the above process for each candidate molecule and further comprising the step e) of comparing the affinity of each candidate molecule quantified in step d) to the one of the other candidate molecules.

Another object of the present invention is a process for determining the affinity of ligand molecules that specifically bind to the NEP binding site for the QHNPR (SEQ ID NO: 2) pentapeptide, comprising the steps of:

a) preparing a cell culture or preparing an organ specimen or a tissue sample (cryosections or slices or membrane preparations or crude homogenates) containing NEP binding sites for the QHNPR (SEQ ID NO: 2) pentapeptide;

b) adding the candidate molecule which has previously been labeled with a radioactive or a nonradioactive label;

c) incubating the cell culture, organ specimen or tissue sample of step a) in the presence of the labeled candidate molecule during a time sufficient and under conditions for the specific binding to take place; and d) quantifying the label specifically bound to the cell culture, organ specimen or tissue sample in the presence of various concentrations of the labeled candidate molecule (preferably $10^{-10}$ to $10^{-5}$ M).

The candidate ligand molecule may be radioactively labeled ($^{32}P$, $^{35}S$, $^{3}H$, $^{125}I$ etc.) or nonradioactively labeled (biotin, digoxigenin, fluorescein etc.)

Thus, the present invention also pertains to a process for screening ligand molecules that possess an agonist biological activity on the NEP binding site of the QHNPR (SEQ ID NO: 2) pentapeptide, comprising the steps of:

a) preparing a cell culture or preparing an organ specimen or a tissue sample (cryosections or slices or membrane preparations or crude homogenates) containing NEP binding sites for the QHNPR (SEQ ID NO: 2) pentapeptide;

b) incubating the cell culture, organ specimen or tissue sample of step a) at concentrations allowing measurement of NEP enzymatic activity under initial velocity conditions as defined by the method of Example 1 (Material and methods) in the presence of the candidate molecule (preferably $10^{-10}$ – $10^{-5}$ M), a half-saturating concentration of QHNPR (SEQ ID NO: 2) and a NEP substrate during a time sufficient for the hydrolysis of the NEP substrate to take place under initial velocity conditions;

c) quantifying the activity of the NEP present in the biological material of step a) by measuring the levels of NEP substrate hydrolysis, respectively in the presence or in the absence of the candidate ligand molecule and in the presence or in the absence of QHNPR (SEQ ID NO: 2).

In said above process, a half-saturating concentration is the concentration of the QHNPR (SEQ ID NO: 2) pentapeptide which reduces by half the degradation of the NEP substrate.

Another object of the present invention comprises a process for screening ligand molecules that possess an antagonist biological activity on the NEP binding site of the QHNPR (SEQ ID NO: 2) pentapeptide, comprising the steps of:

a) preparing a cell culture or preparing an organ specimen or a tissue sample (cryosections or slices or membrane preparations or crude homogenates) containing NEP binding sites for the QHNPR (SEQ ID NO: 2) pentapeptide;

b) incubating the cell culture, organ specimen or tissue sample of step a) at concentration allowing measurement of NEP enzymatic activity under initial velocity conditions in the presence of a submaximal concentration of the XQH-NPR (SEQ ID NO: 10) peptide, specifically the QHNPR (SEQ ID NO: 2) peptide and a NEP substrate, in the presence of the candidate molecule during a time sufficient for the hydrolysis of the NEP substrate to take place under initial velocity conditions;

c) quantifying the activity of the NEP present in the biological material of step a) by measuring the levels of NEP substrate hydrolysis, respectively in the presence or in the absence of the candidate ligand molecule and in the presence or in the absence of QHNPR (SEQ ID NO: 2).

In a preferred embodiment of said above process, a submaximal concentration is a concentration of pentapeptide which reduces by at least 50% and preferably by at least 75% the degradation of the substrate.

As mentioned above, another metabolic assay in order to assess the agonist or the antagonist activity of the candidate ligand molecule comprises the incubation of the ligand candidate in the presence of a primary cell culture or established cell line or tissue sample of rat, mouse or human origins and an endogenous or exogenous NEP substrate and determining, either or both quantitatively and qualitatively, the hydrolysis of the NEP substrate.

A preferred tissue sample that is used in the screening methods according to the present invention is a membrane preparation or slices of spinal cord from rats, a tissue known to be appropriated for NEP activity measurement.

Other preferred tissue samples that can be used in the screening methods according to the present invention are all peripheral tissue preparations that are known to be enriched in NEP-peptidase and/or to be targets for SMR1-peptide, for example rat renal outer medulla, placenta, testis, prostate and bone and dental tissues. In addition, such a procedure can also be applied to tissues and/or cells of mammals (e.g. mouse) and especially human origin or cell lines transfected with human NEP cDNA, for example MDCK, HEK or COS cells first transfected with human NEP cDNA.

Preferred biologically active derivatives of SMR1-peptide and specially of $X_1QHX_2X_3X_4$ (SEQ ID NO: 11) of the therapeutic composition according to the present invention have better pharmacodynamic properties than the endogenous natural or synthetic $X_1QHX_2X_3X_4$ (SEQ ID NO: 11) peptide, and thus possess a longer in vivo half-life as compared to their natural counterparts and a better bioavailability in a given tissue/space, especially in nervous, intestine, placental and gonad tissues.

The above-described biologically active derivatives, are also an object of the present invention.

Thus, the invention also relates to the SMR1 maturation products and the biologically active derivatives of the SMR1 protein or of its maturation products that can be selected according to the screening processes hereinbefore described, provided that they have not the structure of formula (1) above. Indeed, also excluded, is the 146 amino acid protein constituting the SMR1 protein itself (PCT Patent Application No WO 90/03981). However, the therapeutic use of these molecules that are excluded as such of the present invention, is a main object of the instant invention.

Another object of the present invention is a biologically active derivative of the SMR1-peptide characterized by its capacity either to increase or decrease a metallopeptidase activity or to prevent the normal interaction between the SMR1-peptide and said metallopeptidase. Preferably, said metallopeptidase is a membrane-zinc metallopeptidase. More preferably, said membrane-zinc metallopeptidase is NEP.

The biologically active derivatives of SMR1-peptide so characterized also include SMR1 protein maturation products, provided that they do not have the structure of formula (1) above.

The SMR1 protein or its maturation products and the biologically active derivatives of the SMR1 protein or of its maturation products used in the therapeutic compositions according to the present invention have been, in a preferred embodiment, selected firstly according to their ability to bind to the same targets as the $X_1QHX_2X_3X_4$ (SEQ ID NO: 11), specifically QHNPR (SEQ ID NO: 2) peptide, and secondly by their capacity to modulate hydrolysis of substrate of a metallopeptidase for example the NEP in vitro or in vivo.

By "modulate", it is understood that said SMR1-peptide has the capacity either to increase or decrease (inhibit) the metallopeptidase activity or to prevent the normal interaction between the SMR1-peptide and the said metallopeptidase.

The present invention also deals with the use of therapeutic compositions comprising an effective amount of the SMR1-peptide.

In the methods according to the invention, the peptides or peptidomimetics according to the invention may be administered by any of a variety of means. In certain preferred embodiments, administration may be parenteral, most preferably intravenous. In other preferred embodiments, administration may be intranasal, oral, sublingual, transmucosal, intrarespiratory, or through an inert or iontophoretic patch.

Dosages of the peptide or peptidomimetic to be administered will depend on the particular patient, the condition, and the route of administration, and can be determined empirically by the reduction or elimination linked to the pathological disorders listed above in response to an elevating dosage regimen. Preferred dosages are from about 0.1

μg/kg to about 1 mg/kg, more preferably from about 1 μg/kg to about 100 μg/kg, and most preferably from about 1 μg/kg to about 50 μg/kg.

In certain preferred embodiments, the peptide or peptidomimetic according to the invention is administered together with a second pharmaceutical, wherein the second pharmaceutical agent is present in an amount insufficient to reduce or eliminate symptoms of the disorder or disease to be treated, and wherein the peptide or peptidomimetic according to the invention and the second pharmaceutical agent act synergistically to reduce or eliminate symptoms of the disorder or disease to be treated. Such second pharmaceutical agent may or may not act as a modulator of the metallopeptidase.

"Synergistically" means that the peptide or the peptidomimetic and the second pharmaceutical agent together are more effective in reducing or eliminating symptoms of a disorder or disease than either one alone would be at the same concentration.

The present invention also relates to a molecular complex comprising:
the NEP receptor or the SMR1-binding site of the NEP receptor;
the SMR1-peptide.

The present invention is illustrated in details in the following examples without being in any way limited in scope to these specific embodiments.

BRIEF DESCRIPTION OF THE DRAWINGS

FIG. 1-B: Time course of Substance P hydrolysis (12.5 nM) by rat spinal cord membrane preparations in the presence or absence of different peptidase inhibitors at 10 μM final concentration:—an ACE inhibitor, captopril,—the CPB and DPPIV inhibitors, GEMSA and DPPIV inhibitor. Each point represents the percent of 3H-substance P hydrolyzed by 250 μg membrane proteins incubated at 25° C. in a 250 μl final volume of Tris/HCl buffer.

FIG. 2-B: Values represent the quantity of intact Met-enkephalin (mean of 2 determinations) determined by RP-HPLC analysis (peak height at 18.9 min. Retention time) recovered after 20 min. incubation at 25° C. with 1 mg fresh tissue slices in a 1 ml final volume of KRBG buffer.

FIG. 3-B: Concentration-dependent inhibition by SMR1 QHNPR (SEQ ID NO: 2) of 3H-Substance P (12.5 nM) catabolism by rat spinal cord membrane preparations. Comparison with—a NEP inhibitor, Phosphoramidon and,—CPB and DPPIV inhibitors, GEMSA+DPPIV inhibitor. Comparison between the inhibitory activity exerted by QHNPR (SEQ ID NO: 2) peptide alone or in combination with CPB and DPPIV inhibitors. Each point represents the mean recovery (in percentages) of intact 3H-substance P after 10 min; incubation at 25° C. with 250 μg membrane protein in 250 μl Tris/HCl buffer (mean of 2 determinations).

FIG. 4-A: Endopeptidase activity of the tissue membrane preparations was determined using 25 nM [3H] substanceP, in the presence of 10 μM bestatin. The enzymatic specific activity expressed in pM/min/μg membrane protein is done in the absence and in the presence of 10 μM sialorphin or NEP inhibitors (10 μM phosphoramidon or 1 μM thiorphan).

FIG. 4-B: Concentration-dependent inhibition by sialorphin of [3H] substanceP catabolism by rat renal membrane preparations. Each point represents the percentage of 320 nM intact [3H] substanceP recovered and calculated as percentage of velocity without inhibitor—velocity in presence of inhibitor/velocity without inhibitor, and (*) represents the mean±SD of four determinations. Sialorphin concentration is expressed in nM and plotted on a log scale in B right. The protein concentration of membrane enzyme were defined according to conditions of measurement of initial velocity.

Figures 5A, 5B, 5C:
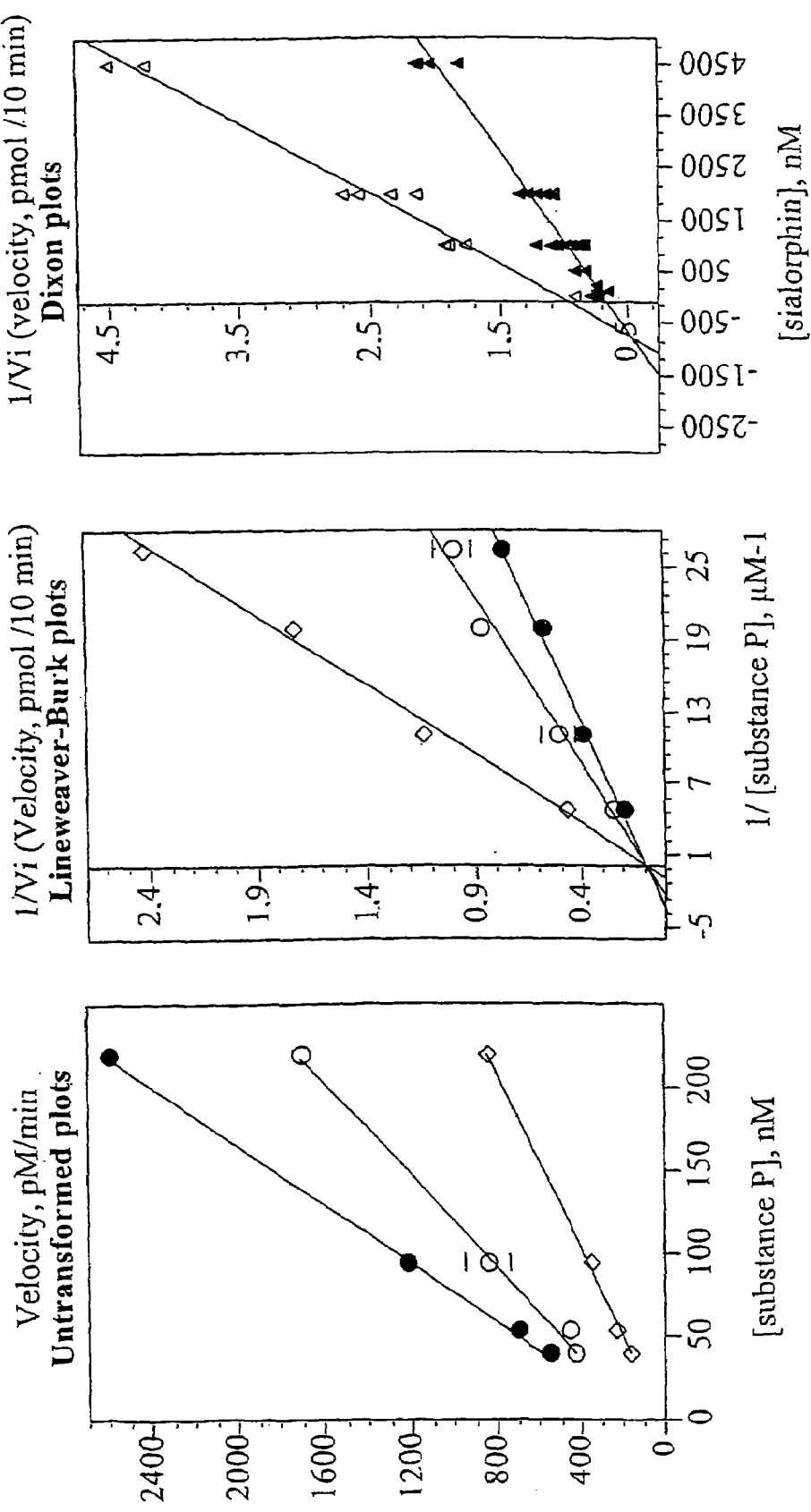
FIGS. 5 A, B and C: Representative profiles of untransformed (FIG. 5-A) and double reciprocal (FIG. 5-B) and Dixon (FIG. 5-C) plot analysis of the inhibitory activity of sialorphin on substance P-endoproteolytic activity by rat renal membranes.

The inhibitory potency of sialophin was measured by using substance P as substrate at concentrations indicated for A and B, and at 14–24 nM (blank triangle) or 56–105 nM (black triangle) for FIG. 5-C. Concentrations of inhibitor for FIG. 5-A and FIG. 5-B were 0 (black circles), 1500 (blank circle) and 4500 nM (blank diamond). Each point of the untransformed and double reciprocal plots represents the mean of 2 independent determinations of duplicate. Experiments were performed at 25° C. in 250 μl Tris-HCl buffer (50 mM pH 7.4) under initial velocity measurement conditions.

Figure 6A:
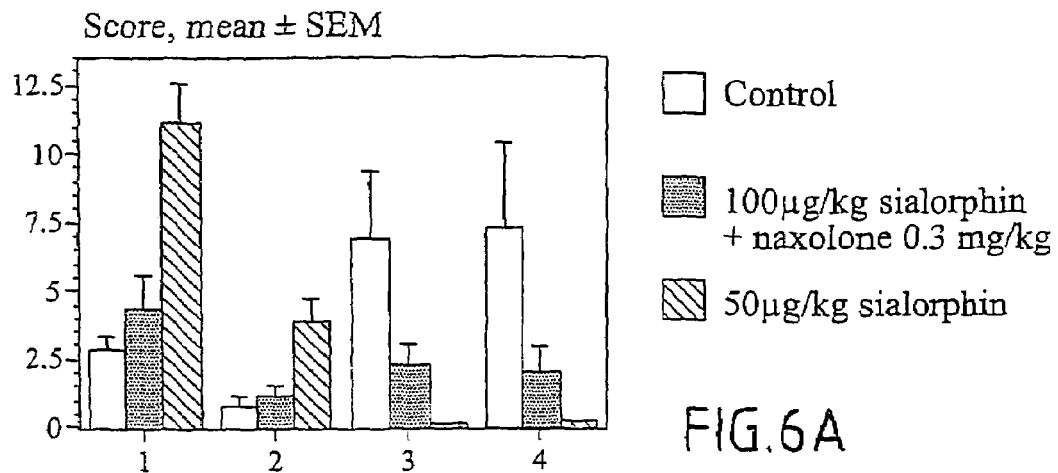
Figure 6B:
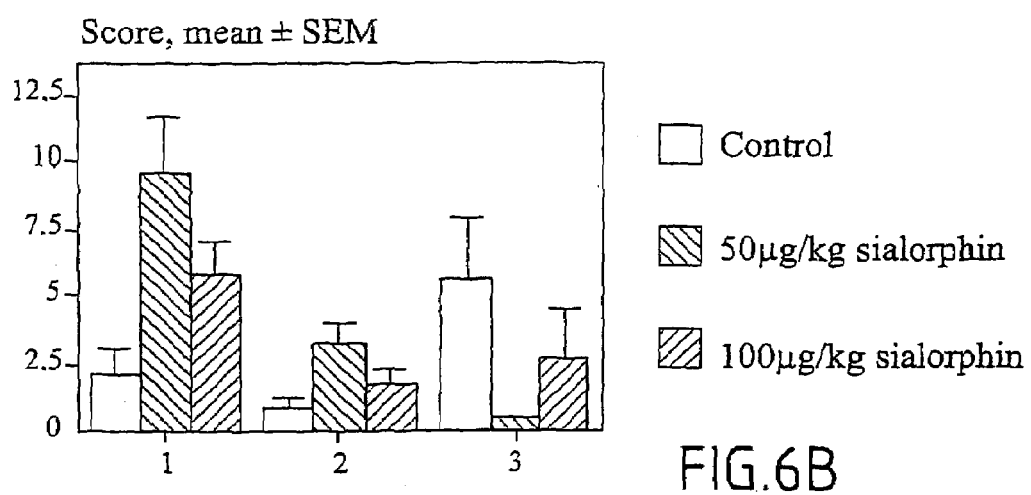
Figure 6C:
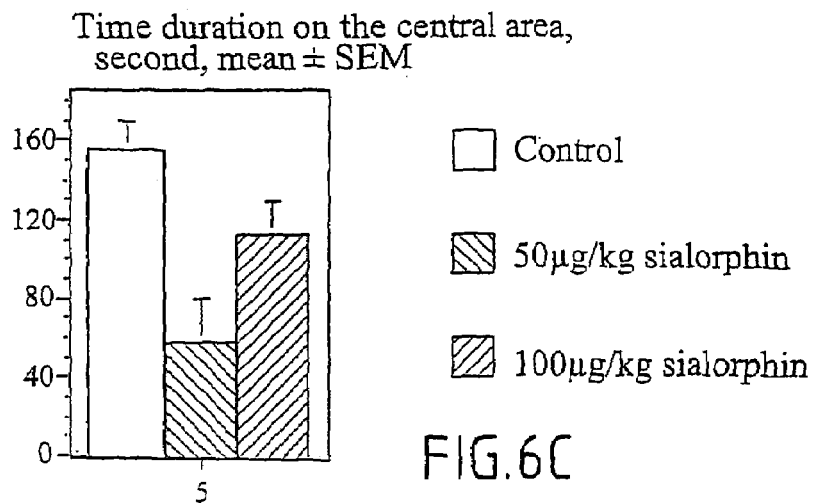

FIGS. 6 A, B and C: Pain responsiveness to a noxious stimulus in rats following intravenous administration of sialorphin.

The 3-min test session was performed 5 min after intravenous. rat tail vein administration of sialorphin or its vehicle. Naloxone (0.3 mg per kg body weight) was injected subcutaneously 15 min before sialorphin administration. Time in centre field sector (FIG. 6-C) (central square of the open-field without pin) and activity (FIGS. 6-A and 6-B) in peripheral squares (overlayed with pins) during the 3-min test session. Each value represents the mean±sem of 8 animals per group. 1=number of crossings of peripheral squares; 2=rearing number on peripheral squares; 3=number of escapes responses; 4=number of audible vocalisation and 5=time displayed in the central area. Control group corresponded to pain response in vehicle-treated rats. 50 µg/kg sialorphin, 100 µg/kg sialorphin, 100 µg/kg sialorphin plus naloxone 0.3 mg/kg.

EXAMPLES

Example 1

Ex vivo, Exploration of the Functional Consequences Resulting from the Interaction of SMR1-QHNPR (SEQ ID NO: 2) Peptide with NEP The consequences of the protection of exogenous NEP-sensitive peptides by SMR1-Pentapeptide, in the extracellular levels of Met-Enkephalin and Substance P have been assessed using membrane preparations and fresh slices of rat nervous tissues.
1. Materials and Methods
1.1. Animals and Tissue Preparations
Sexually mature (from 7 to 9 weeks) male Wistar rats (Iffa Credo), were used. Up to the day of experiment, the rats were kept under conditions of constant ambient temperature (24° C.) and of cycled light (on 8 h/off 20 h) with distribution of food and water ad libitum. On the day of the experiment, the animals were sacrificed by cardiac puncture under pentobarbital (Sanofi, 45 mg/kg body weight, i.p.) or ketamine (Imalgene 500, Rhone Merieux, 150 mg/kg body weight, i.p.) anesthesia or alternatively by carbon dioxide asphyxia.

Slices of Fresh Tissue

The organs are rapidly removed, dissected on ice, freed of nerve fibers and of adipose tissues and then washed in cold oxygenated glucose- and bicarbonate-containing Krebs Ringer (KRBG) solution, whose composition is the following: 120 mM NaCl-5 mM KCl-1.2 mM $KH_2PO_4$-27.5 mM $NaHCO_3$-2.6 mM $CaCl_2$-0.67 mM $MgSO_4$-5.9 mM glucose. The slices of tissues are prepared either manually with the aid of a scalpel (1–2 mm thick), or mechanically with the aid of a "Tissue Chopper" (1 mm thick). Slices are then dispersed into reaction tubes where they are subjected to three successive washes in ice-cold oxygenated KRBG. Thereafter, they are kept at 4° C. in the same buffer supplemented with 10 µM Bestatin (a membrane aminopeptidase, (APN), inhibitor, Roche) and oxygenated under an atmosphere of 95%O2-5% $CO_2$ until used immediately, as enzyme source.

Membrane Preparations

The organs dissected out and washed in ice-cold KRBG are homogenized at 4° C. in 10 volumes (vol./wt.) of 50 mM Tris/HCl buffered at pH 7.2, using a Teflon-glass homogenizer (3×5 sec.). A first centrifugation of 5 min. at 1000×g and 4° C. makes it possible to remove the tissular debris and the nuclei in the pellet. A second centrifugation of the supernatant at 100 000×g and 5° C. concentrates the membrane fraction into the pellet, which will be superficially washed three times with cold Tris/HCl buffer and resuspended in fresh buffer using a Kontes homogenizer, aliquoted and stored at −80° C. while waiting to be used as enzyme source, at least until three months.

1.2 Protein Determination

For the determination of the tissue and membrane protein concentrations, the Bio-Rad DC protein assay (Bio-Rad), was used. As with the Lowry assay, the Bio-Rad kit is based on the reaction of sample protein content with an alkaline copper tartrate solution and Folin reagent. The absorbance is read at 750 nm from 15 min. to 2 h. after the addition of reagent. The calibration curve is prepared from dilutions of a standard solution of BSA (Bovine Serum Albumin) from 0.2 to 1.44 mg/ml protein.

1.3. Measurement of the NEP Enzymatic Activity 1.3.1. NEP Source—Substrates and Inhibitors For the experiments of analysis of the NEP peptidase activity, an ex vivo model using incubations of membrane and fresh tissue slice preparations from nervous tissues that are known to be appropriate for exploring NEP peptidase activity: i.e. the dorsal zone of rat spinal cord, was first developed. The metabolism rate of the NEP-sensitive peptides was measured using the both NEP substrates involved in the signaling of the nociceptive response: the neuropeptides Met-enkephalin and Substance P. Native Met-enkephalin (Peninsula, 10 µm) and modified tritiated Substance P: [(3,4³H) $Pro^2$-$Sar^9$-$Met(O_2)^{11}$]-Substance P with a specific radioactivity of 40 Ci/mmol. (NEN, 12.5–25 nM) were used.

The objective was to measure the NEP-specific endoproteolysis of these substrates. For that, in each test, the hydrolysis of substrate both in the presence and in the absence of specific synthetic inhibitors of NEP (10 µM Phosphoramidon, Roche and/or 1–10 µM Thiorphan, Sigma), and in all cases in the presence of an inhibitor of APN, the Bestatin (10 µM) was analysed. Furthermore, for studying the functional role of SMR1-QHNPR (SEQ ID NO: 2), the reaction was carried out in the presence of the SMR1-peptide alone or combined with specific inhibitors of membrane peptidases which could inactivate the QHNPR (SEQ ID NO: 2) peptide by cleaving its C-terminal end: an inhibitor of carboxypeptidase B (GEMSA, 10 µM, Sigma) and an inhibitor of dipeptidylpeptidase IV (DPPIV inhibitor, 10 µM, Roche).

1.3.2. The Enzymatic Activity Assay

Slices of Fresh Tissue

In the first instance, sections of fresh tissue are preincubated in KRBG medium containing 10 µM bestatin, at 25, 30 or 37° C. in a constantly shaken water bath and under an atmosphere of 95%O2-5% CO2, in the presence or in the absence of NEP inhibitor. At the end of the preincubation period (15 min.), the medium is replaced with fresh medium containing the substrate alone or combined with NEP inhibitor or SMR1-QHNPR (SEQ ID NO: 2) and the incubation is carried out at the same incubation conditions as the preincubation. At the end of the incubation period (from 5 to 30 min.), the medium is transferred to ice-cold tubes containing hydrochloric acid, such as the final concentration of HCl will be 0.1 N. Samples are kept at −30° C. until the measurement of their intact substrate and its metabolites content.

The temperature and time of incubation as well as the concentration of substrate and of tissue enzyme are defined according to the results such as the NEP hydrolysis activity will be measured under conditions of initial velocity.

Membrane Preparations

The membrane preparations are preincubated in 50 mM Tris/HCl buffered at pH 7.2 and containing 10 µM Bestatin, at 25, 30 or 37° C. in constantly shaken water, in the presence or in the absence of NEP inhibitor. At the end of the preincubation period (10 min), the substrate is added alone or combined with NEP inhibitor or SMR1-QHNPR (SEQ ID NO: 2) and the incubation is carried out at the same incubation conditions as the preincubation. At the end of the incubation period, the reaction is stopped by cooling to 4° C. and adding to hydrochloric acid such as the final concentration of HCl will be 0.3 N. Samples are kept at −30° C. until the measurement of their intact substrate and its metabolites content.

The temperature and the time of the incubation as well as the concentration of substrate and of membrane enzyme are defined according to the results such as the NEP hydrolysis activity will be measured under conditions of initial velocity.

1.3.3. The Detection of the Substrate and its Metabolites

To separate, detect and quantify the intact substrate and its metabolites, various techniques (depending on whether the substrate was radiolabeled or not), were used: two are based on the principle of reverse-phase chromatography for the selective isolation of the products of the reaction (C-18 Sep-Pak cartridges and RP-HPLC) and the third is based on the specific detection of the substrate by radio-immunoassay (RIA).

The C-18 Sep-Pak Cartridges

The C-18 Sep-Pak cartridges (Waters) were used to analyze the hydrolysis of the radiolabeled peptides: they separate compounds according to their differences in polarity. This solid-phase extraction procedure allows isolating the substrate from its metabolites, since the hydrophobic character of the peptide metabolites is reduced or even lost compared to the intact peptide substrate.

3H-Metabolites of radiolabeled substance P are eluted in two steps: one with $H_2O$—0.1% TFA and the second one with 20% methanol—0.1% TFA, while the intact 3H-substance P is eluted in the third step with 70–100% methanol-0.1% TFA. The radioactivity of eluted and isolated compounds is determined by liquid scintillation spectrometry.

RP-HPLC (Reverse Phase High Performance Liquid Chromatography)

HPLC is a highly resolutive procedure that allows the isolation and detection by coupled spectrophotometer analysis, of the non-radioactive peptides whose concentration is at least 1 to 10 μM. The C-18 RP-HPLC is based on the same principle as the C-18 Sep-Pak cartridge. The chromatographic analyses were used to study the hydrolysis of Met-Enkephalin, that were done on a C-18 LUNA analytical column (150×4.6 mm inner diameter, AIT) packed with 5 μm-diameter beads.

RP-HPLC performed with a one-step 30-minute linear gradient ranging from $H_2O$—0.1% TFA to 100% acetonitril—0.1% TFA, at a 1 ml/min flow rate, leads to a resolutive separation of the two Met-Enkephalin metabolites and of the intact substrate. Their identification and relative quantification (peak height) are checked by continuously monitoring the UV absorbance at 254 nm of column outflow.

RIA Assay (Radio-Immuno-Assay)

RIA is a fine analytical method, which allows quantifying compounds, whose concentration is between 1 and 100 nM or even less. Herein, a competitive RIA system has been used: the quantity of radioactive antigen bound to the antibody decreases in a manner inversely proportional to the quantity of antigen contained in the standard solution or in the sample. The free radioactive antigen is separated from the radioactive antigen—antibody complex by immunoprecipitation.

The activity of enkephalinase NEP is monitored by quantification of the disappearance of the initial Met-enkephalin substrate. The first antibody used is a rabbit antibody directed against the C-terminal end of Met-enkephalin (cross-reactivity with metabolites or other peptides is $\leq 1\%$) (Goros et al, J. Neurochem. (1978), 31; 29–39. Radio immunoassay of methionine and leucine enkephalins in regions of rat brain and comparison with endorphins estimated by a radioreceptor assay). The second antibody is a horse antibody directed against the rabbit immunoglobulins. The radiolabeled antigen is iodinated Met-enkephalin ($^{125}$I-Met-Enk enkephalin) with a specific radioactivity estimated at 3000 Ci/mmol.

Briefly, the Met-enkephalin RIA is performed in 100 mM Tns/HCl buffered at pH 8.6 and containing 0.1% BSA and 0.1% Triton X 100. Standard (1–100 nM) or sample (100 μl), diluted anti-Met-Enkephalin antibody (100 μl, 1/2000) and $^{125}$I-Met-Enk (10000 cpm, 100 μl) are incubated overnight at 4° C. Bound and free fractions are separated by immunoprecipitation with the second anti-rabbit immunoglobulin in presence of polyethylene glycol 6000 (6%). After centrifugation, the bound radioactivity of the precipitate is quantified using a gamma-spectrometer.

2. Results

To specify the inhibitory role of the SMR1-QHNPR (SEQ ID NO: 2) on the NEP enzymatic activity, it was necessary to first develop an experimental protocol allowing to perform the hydrolysis of Substance P or Met-Enkephalin peptides under conditions of initial velocity measurement.

2.1. Search for Experimental Conditions of Initial Velocity Measurement of NEP Endopeptidase Activity 2.1.1. Hydrolysis of Native Met-Enkephalin In first series of experiment, the slices and the membrane preparations of spinal cord tissues were incubated at 30° C. in a 1 ml final volume of KRBG, and at 37° C. in a 0.25 ml final volume of Tris/HCl 50 mM, pH 7.2, respectively.

RP-HPLC Analysis

The calibration of the RP-HPLC chromatographic system reveals that marker Met-enkephalin is eluted at a retention time of 18.8 min. In the case of the samples, a peak is identified whose height increases considerably in the presence of a NEP-specific inhibitor: this peak, whose retention time is 18.8±0.2 min., corresponds to the intact Met-enkephalin substrate. Conversely, two peaks having retention times of 5.8±0.2 min. and 12.8±0.1 min., corresponding to the metabolites Tyr-Gly-Gly and Phe-Met respectively, appear in the absence of NEP-inhibitors. This result indicates that spinal tissue enzyme has cleaved the substrate predominantly at the $Gly^3$-$Phe^4$ amide bond of the peptide, which already corresponds to enkephalinase activity.

At the level of membrane preparations as well as of fresh tissue slices, a high NEP-specific hydrolysis of the exogenous Met-enkephalin is observed during the 10 min. incubation at 37° C.: the spinal cord enkephalinase activity provokes a disappearance of the Met-enkephalin peak and that is reversed in the presence of 10 μM Phosphoramidon or 1 μM Thiorphan (80–90% inhibition). In addition, under these conditions, both specific NEP inhibitors ensure the almost complete inhibition of enkephalinase activity over the time of incubation at 37° C., from 10 to 30 min.

Since, the maximum hydrolysis was undoubtedly reached, at 37° C. temperature within the 10 min. incubation, in the next experiments the incubation temperature has been subsequently reduced to 30° C. then to 25° C. Effectively, for the fresh tissue slices incubated at 30° C., the level of hydrolysis of Met-enkephalin increases with time (from 0 to 30 min.). In the same manner, for the membrane preparations incubated at 30° C., it is also possible to note an increase in the level of hydrolysis in relation to the enzyme concentration (from 0 to 2 mg/ml). However, no clear linear relationship could be established.

Indeed, the HPLC chromatography coupled to spectrophotometer analysis is a semi-quantitative technique and the single measurement of the heights or areas of peaks is not sufficiently precise to calculate quantitative proportional relationships. Then, to precisely quantify the Met-enkephalin, a specific quantitative RIA detection was used.

2.1.2. Hydrolysis of Modified Tritiated Substance P

The experimental parameters which allow to study, under conditions of initial velocity measurement, the hydrolysis of the substrates, Met-enkephalin and Substance P, by nervous tissue-containing NEP, have been established.

Figure 1A:
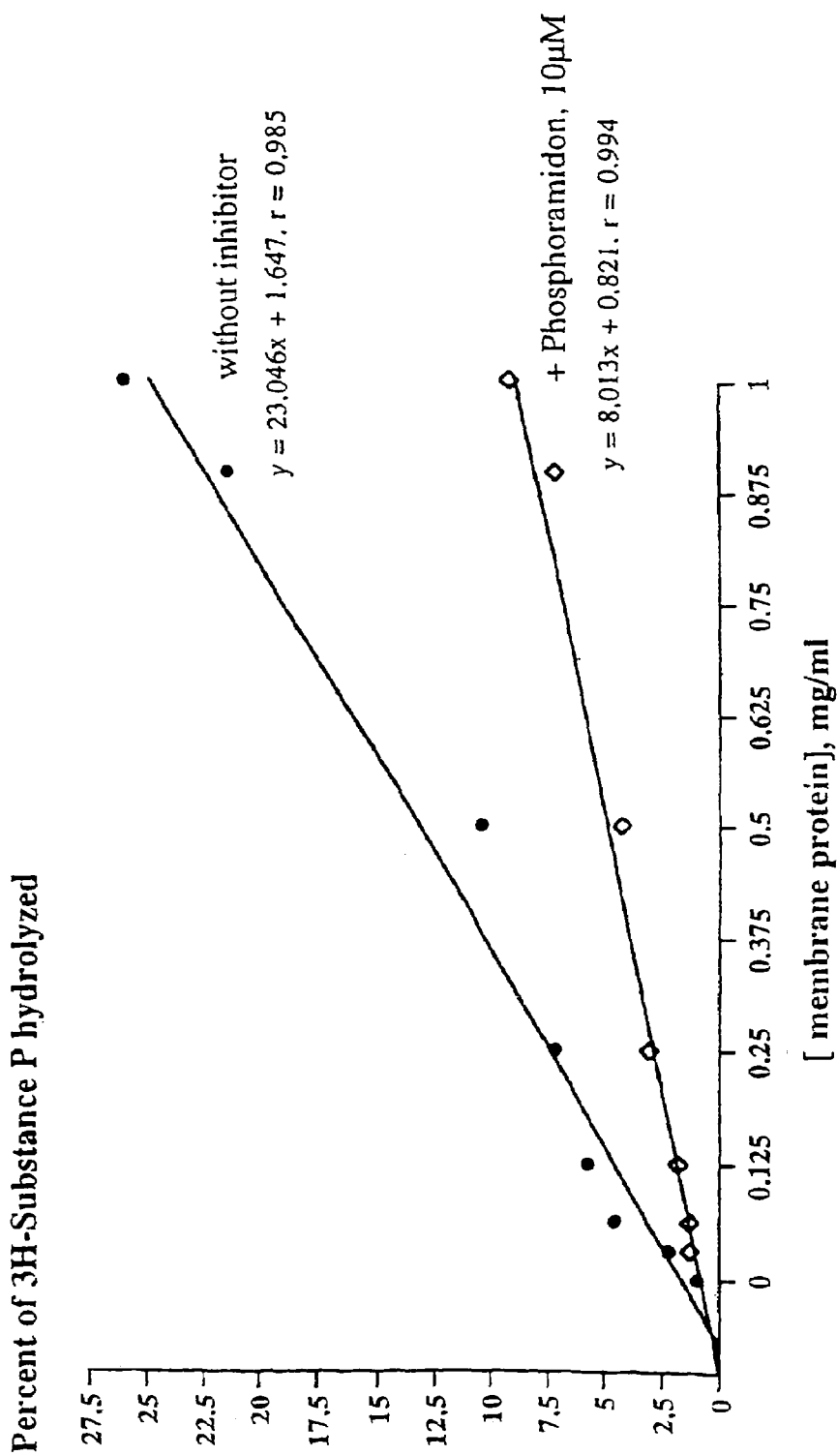
FIG. 1-A: Influence of spinal cord membrane protein concentration on Substance P hydrolysis (25 nM) in the presence or absence of the synthetic NEP inhibitor, Phosphoramidon, 10 μM. Each point represents the percent of 3H-substance P hydrolyzed by spinal cord membrane incubated 15 min. at 30° C. in a 250 μl final volume of Tris/HCl buffer.
Figure 1B:
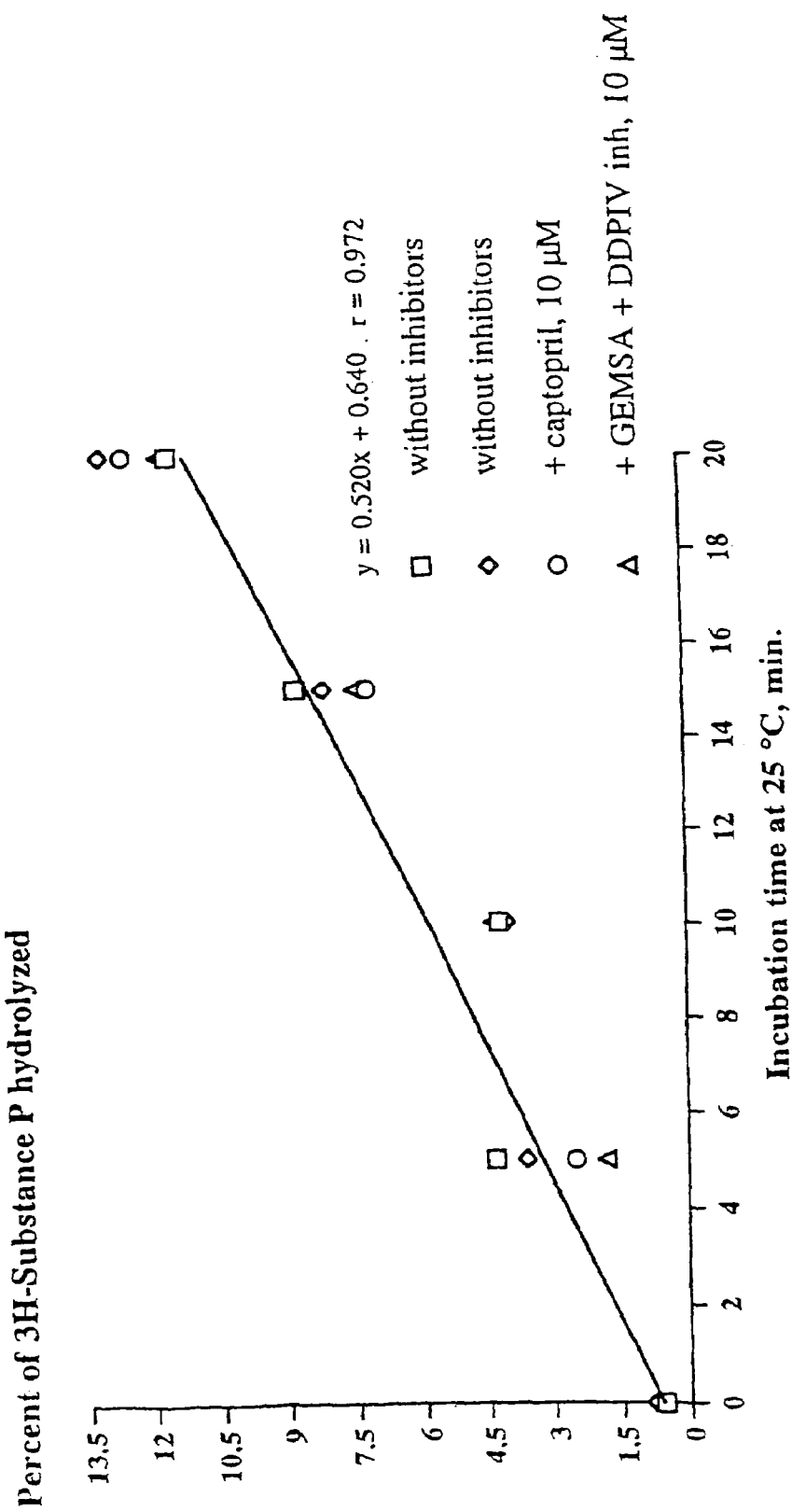

In that respect, the influence of the membrane protein concentration of rat spinal cord (from 0.03 to 1 mg/ml, final concentration) on the level of the Substance P hydrolysis (25 nM), after 15 min. incubation at 30° C., was first tested. As illustrated in FIG. 1-A, the levels of the 3H-Substance P degradation, expressed in percent of initial substrate concentration, increase proportionally from 2 to 25% in a linear related-function to membrane protein concentration. A close correlation of r=0.98, n=7 was found in the absence and, of r=0.99, n=7 in the presence of 10 μM Phosphoramidon. Furthermore, in the same experimental condition, the addition of Phosphoramidon results in a clear reduction of the Substance P degradation (50 to 65% protection of exogenous peptide).

Similarly, the level of Substance P hydrolysis (12.5 nM) as a function of the incubation time at 25° C. (5–20 min) was also studied. The membrane protein concentration chosen was 1 mg/ml. The Substance P catabolism by spinal cord membranes increases linearly with the time of incubation, with a close correlation of r=0.97, n=18 (FIG. 1-B). Captopril, (10 μM) a potent inhibitor of the Angiotensin Converting Enzyme (ACE) which also cleaves the Substance P, has no effect on the activity of the enzyme membrane preparations, as well as, for the potent inhibitors of CPB and DPPIV enzymes (protective compounds of the C-terminal SMR1-QHNPR (SEQ ID NO: 2) potential catabolism).

The conditions of initial velocity measurement of the Substance P hydrolysis by spinal cord tissue containing-NEP therefore appear to be established. However, the activity of both NEP inhibitors (Phosphoramidon and Thiorphan), does not appeared to be proportionally stable as a function of the incubation duration. Accordingly, the effect of the SMR1-QHNPR (SEQ ID NO: 2) peptide on the NEP activity will be systematically studied in relation to the time of incubation.

2.1.3. Record

The experimental conditions that allow study, under initial velocity measurement, of the Met-enkephalin and Substance P catabolism by spinal tissues ex vivo, are reported in the table hereunder.

| | |
|---|---|
| Preincubation time | 10 min (membrane preparations) |
| | 15 min (fresh tissue slices) |
| Incubation times | 5 min to 30 min. |
| Temperature | 25° C. |
| Final concentration of membrane or tissue protein (spinal cord) | 1 mg/ml |
| Substrate concentration | Substance P: 12.5 nM |
| | Met-enkephalin 10 μM (HPLC) |
| | 20 nM (RIA) |
| Reaction volume | 1 ml (fresh tissue slices) |
| | 250 μl (membrane preparation) |
| Technique for separating the Metabolites | Sep-Pak + Liquid scintillation counter (3H-Substance P) |
| | RP-HPLC and RIA (Met-enkephalin) |
| Buffer | Trls.HCI 50 mM, pH 7.2 + BSA 0.1% + Bestatln 10 μM (membrane preparations) |
| | KRBG + BSA 0.1% + Bestatin 10 μM Oxygenated under 95% 02–5% $CO_2$ (Fresh tissue slices) |

2.2 Study of the Functional Consequences Resulting from the Interaction of the SMR1-QHNPR (SEQ ID NO: 2) Peptide with NEP

2.2.1 Degradation of Met-Enkephalin by NEP Spinal Cord

The effect of a fixed concentration of SMR1-QHNPR (SEQ ID NO: 2) (10 μM) on the Met-enkephalinase activity of spinal cord slices under experimental conditions defined in paragraph 2.1.3, was first tested.

RP-HPLC Analysis

Figure 2A:
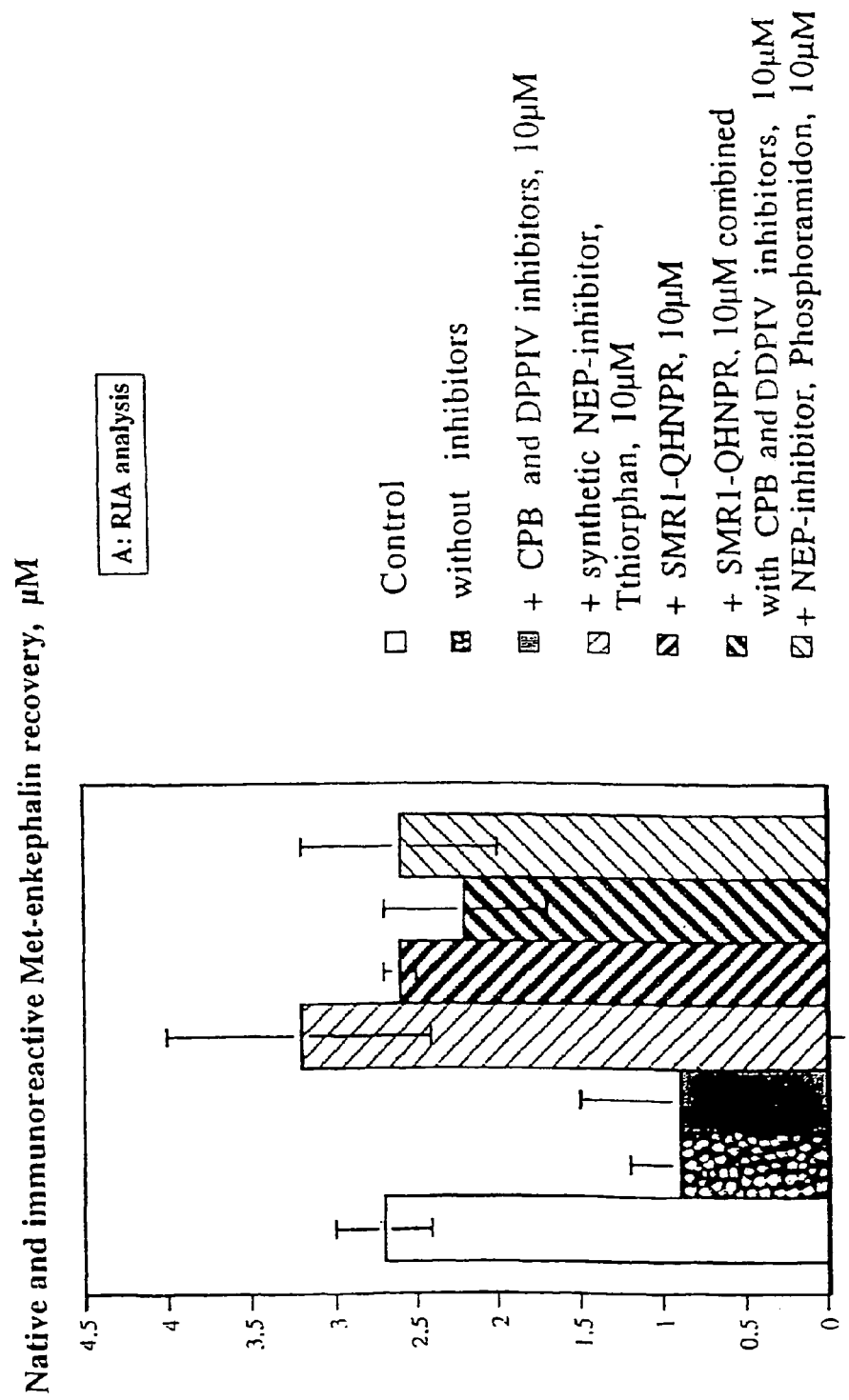
FIGS. 2A and B: Met-enkephalinase activity in spinal cord slices, in the presence or absence of different peptidase inhibitors at 10 μM final concentration:—a NEP inhibitor, Phosphoramidon,—a NEP inhibitor, Thiorphan,—the CPB and DPPIV inhibitors, GEMSA and DPPIV inhibitor,—the SMR1-QHNPR (SEQ ID NO: 2) alone or combined with CPB and DPPIV inhibitors. Control represents the Met-enkephalin recovery in the absence of tissue slice.
Figure 2B:
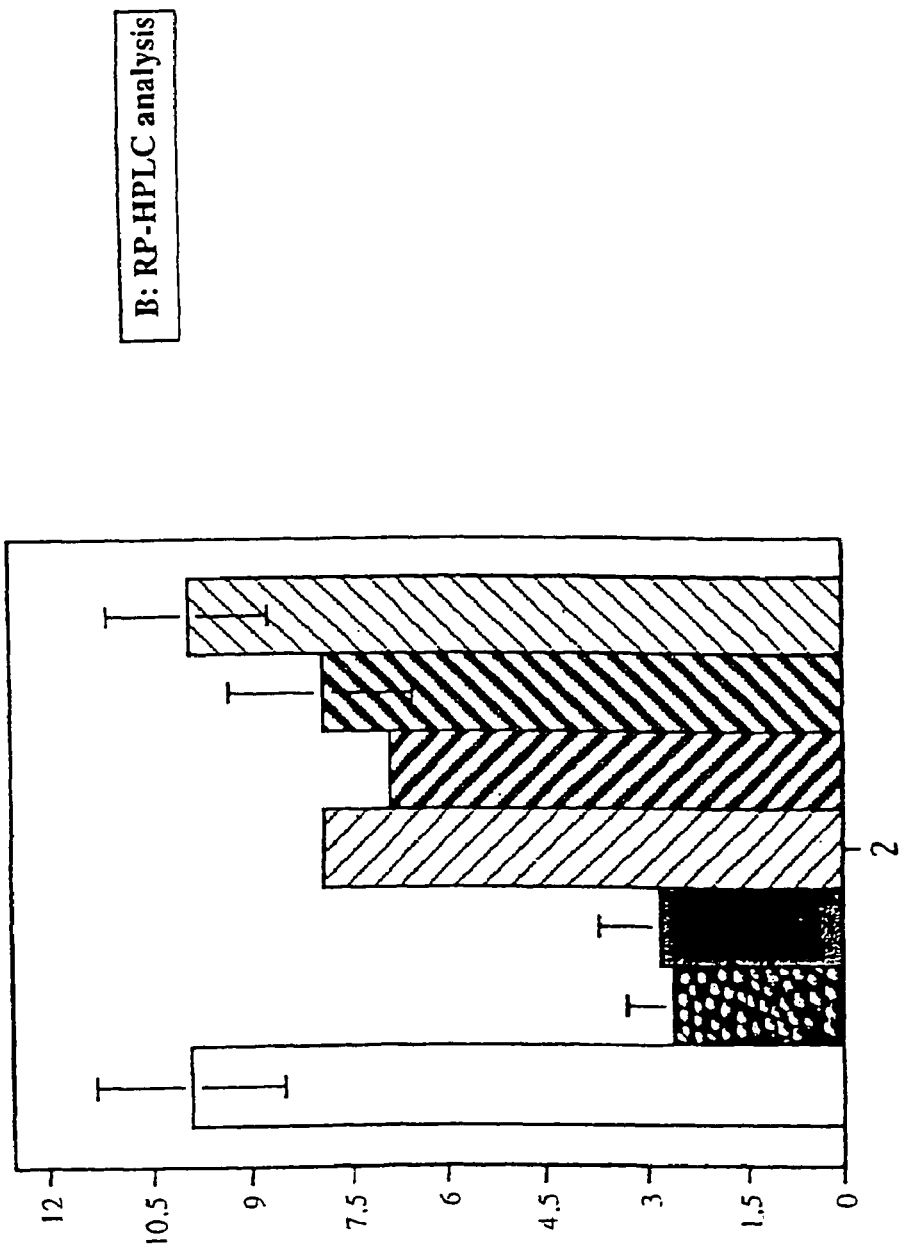
FIG. 2-A: Values represent the concentration of intact and immunoreactive Met-enkephalin (mean of 2 determinations) determined by RIA analysis (μM) and recovered after 20 min. incubation at 25° C. with 1 mg fresh tissue slices in a 1 ml final volume of KRBG buffer.

As illustrated in FIG. 2-B, the HPLC analyses show a strong NEP-specific hydrolysis of the Met-enkephalin substrate by spinal cord slices within the 20 min. incubation at 25° C. Phosphoramidon at a concentration of 10 μM ensures the complete inhibition of Met-enkephalinase activity and addition of Thiorphan (10 μM) results in a clear reduction by 80% of the Met-enkephalin degradation.

In the same experiment, the QHNPR (SEQ ID NO: 2) peptide, at 10 μM concentration, alone or combined with the inhibitors of CPB and DPPIV proteases, has an inhibitory activity of 70 or 80%; thus the SMR1-Pentapeptide is able to enter into competition with the enkephalin-pentapeptide for the NEP binding sites, both being in equal concentrations. As in case of Substance P degradation by spinal membrane preparations, the inhibitors of CPB and DDPIV alone do not have any intrinsic inhibitory activity on the Met-enkephalin degradation by fresh spinal slices. Furthermore, they apparently are no need for protecting SMR1-QHNPR (SEQ ID NO: 2) itself, especially at its C-terminal end, from the peptidase activity potentially present in slices of fresh spinal tissue.

In order to finely quantify the NEP activity and inhibition, the same experiment has been analyzed with the aid of the specific Met-Enkephalin RIA.

RIA Assay

As a whole, the crude results obtained by the reverse phase-HPLC technique are confirmed by those derived from RIA assay (FIG. 2-A). Within the 20 min incubation period at 25° C., the Phosphoramidon, Thiorphan, as well as SMR1-QHNPR (SEQ ID NO: 2) appear as very potent compounds for protecting Met-enkephalin from NEP degrading activity. Thus, at concentration of 10 μM, they almost totally prevented the degradation of 10 μM Met-enkephalin by fresh spinal cord tissue: 96%, 100% and 96% protection, respectively.

In conclusion, all these results show the negative regulatory role exerted by the SMR1-QHNPR (SEQ ID NO: 2) peptide on the Met-enkephalinase activity of rat nerve tissues, ex vivo.

2.2.2 Degradation of Substance P by NEP Spinal Cord SMR1-QHNPR (SEQ ID NO: 2), an Inhibitor of the NEP Activity on Substance P Catabolism In a first instance, the effect of QHNPR (SEQ ID NO: 2) peptide on the hydrolysis of Substance P was searched as it was already done in relation to Met-enkephalin. For that, spinal cord slices were used and a kinetic over a 30-min. incubation period was performed under the conditions of initial velocity measurement defined in 2.1.3.

Figure 3A:
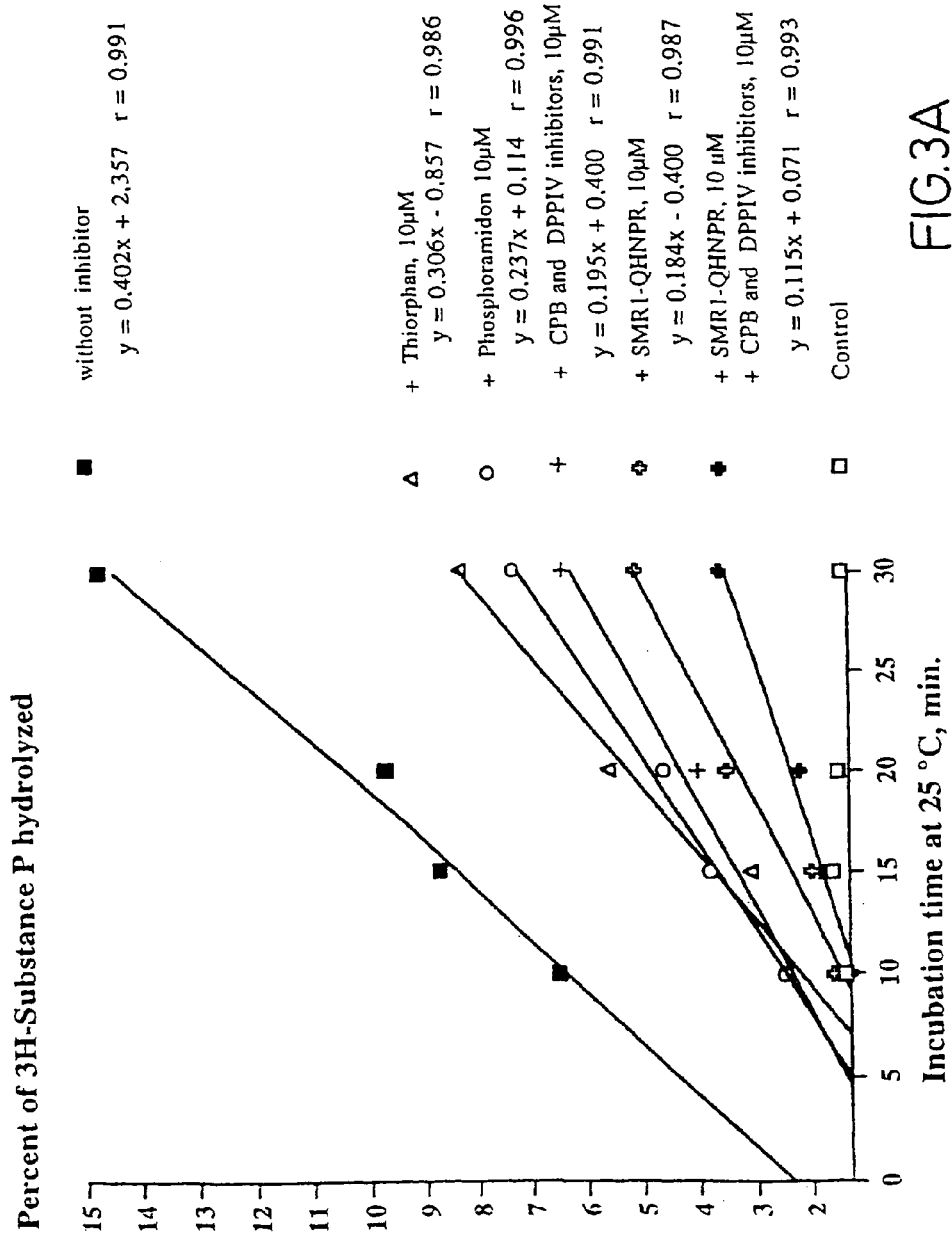
FIG. 3-A: Substance P hydrolysis (25 nM) by rat spinal cord slices, in the presence or absence of different peptidase inhibitors at 10 μM final concentration:—a NEP inhibitor, Phosphoramidon,—a NEP inhibitor, Thiorphan,—the CPB and DPPIV inhibitors, GEMSA and DPPIV inhibitor,—the SMR1-QHNPR (SEQ ID NO: 2) alone or combined with CPB and DPPIV inhibitors. Control represents the 3H-substance P hydrolysis in absence of tissue slice. Each point represents the percent of 3H substance P hydrolyzed by 1 mg fresh tissue slices incubated at 25° C. in a 1 ml final volume of KRBG buffer.
Figure 3B:
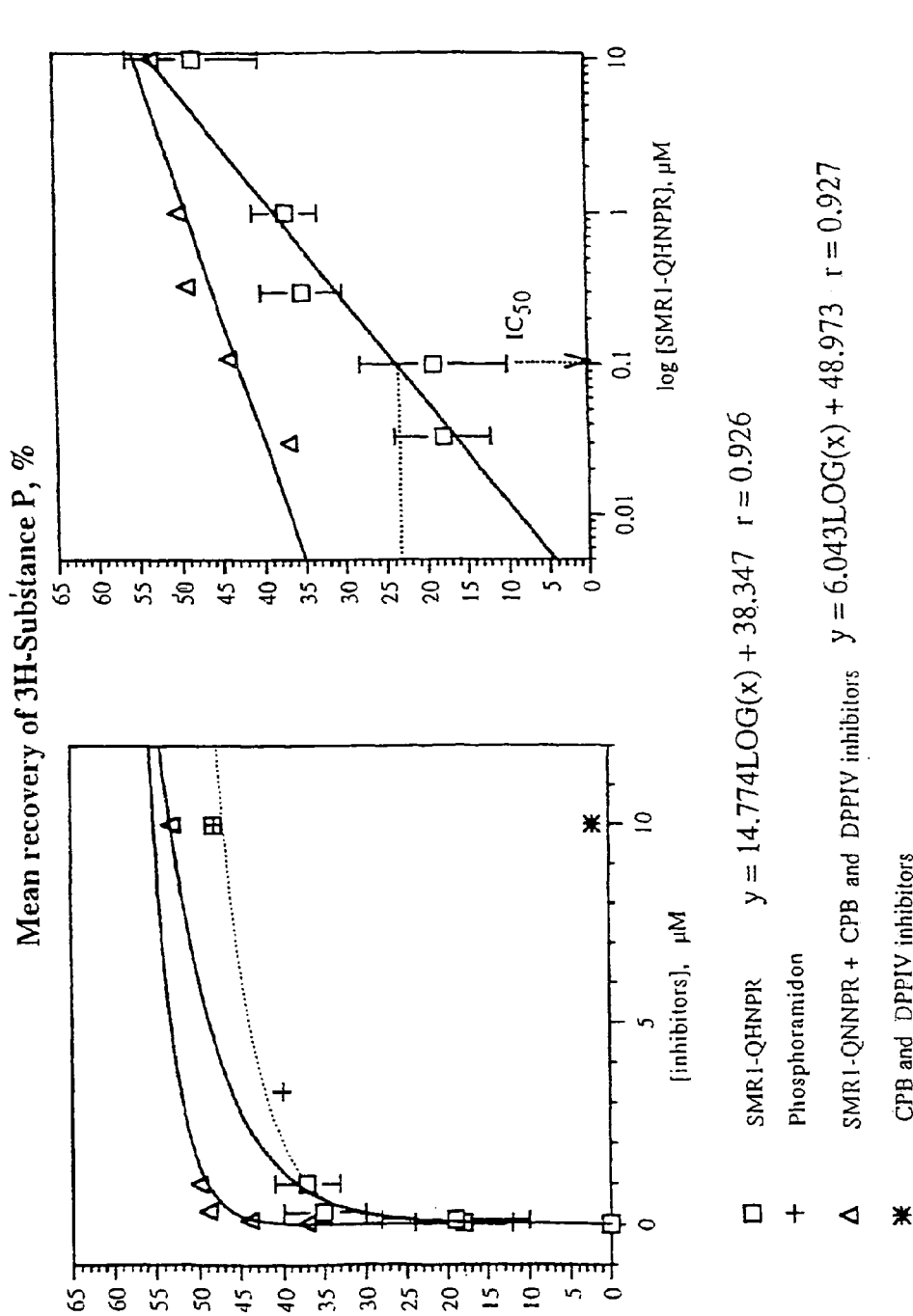

As illustrated in FIG. 3-A, Substance P hydrolysis reaction effectively takes place under initial velocity conditions: a close relationship of r=0.99 was found between the percentage of Substance P hydrolysis and the incubation time at 25° C. Ten μM Phosphoramidon or 10 μM Thiorphan exhibits relatively the same inhibitory activity (60–65% inhibition). The QHNPR (SEQ ID NO: 2) peptide (10 μM) is found to be an efficient inhibitor: 75% inhibition of Substance P degradation when it is alone, more than 90% when it is combined with GEMBA (10 µM) and DPPIV inhibitor (10 µM). These latter, however, appear to exhibit an inherent inhibiting activity of Substance P degradation by fresh spinal tissue.

Otherwise, in this experiment, the effect of inhibitors is proportionally stable as a function of the duration of incubation over the 30 min. incubation period (r=0.99).

Determination of the $IC_{50}$

The dose-response curve of the SMR1-QHNPR (SEQ ID NO: 2) inhibitory effect on 3H-Substance P degradation by spinal cord membrane preparations, shown in FIG. 3-B right panel, allows the calculation of an IC50 value (concentration of the inhibitor reducing by half the degradation of 3H-substance P) of about $1.10^{-7}$ M. In the same experiment, comparison with Phosphoramidon reveals that protection of the exogenous Substance P by SMR1-QHNPR (SEQ ID NO: 2) is still equivalent t0 that obtained with Phosphoramidon (FIG. 3-B left panel). Furthermore, the QHNPR (SEQ ID NO: 2) peptide combined with the inhibitors of CPB and DPPIV exhibits a very high NEP inhibiting activity, greater than that of phosphoramidon (FIG. 3-B, left panel).

2.2.3. Record

The metabolism rate of the NEP-sensitive peptides has been measured using tritiated substrate coupled to chromatographic analysis (Substance P) or using native substrate coupled to specific RIA quantification (Met-enkephalin). Under conditions of initial velocity measurement of the NEP enzymatic activity, an almost complete inhibition of exogenous Met-enkephalin or Substance P catabolism resulting from addition of SMR1-Pentapeptide has been observed: the concentration of SMR1-QHNPR (SEQ ID NO: 2) which reduces by half the degradation of Substance P by spinal cord tissues, was calculated to be $1.10^{-7}$M and its inhibitory potency is equivalent to that of two well-known NEP-specific inhibitors, Thiorphan and Phosphoramidon. From these results it appears that, ex vivo, the SMR1-Pentapeptide efficiently prevents the spinal NEP-induced degradation of both neuropeptides involved in the control of spinal pain perception, e.g. Substance P and Met-Enkephalin.

Example 2

SMR1-QHNPR (SEQ ID NO: 2) (Sialorphin), an Inhibitor of the Substance P-Catabolism by Peripheral Tissues The first results showed the regulatory role exerted by the sialorphin peptide on the enkephalinase activity of rat nerve tissues. The same approach was applied to peripheral tissue membrane preparations that are known to be enriched in NEP-peptidase and/or to be targets for sialorphin, in vivo, i.e., renal outer medulla, intestine mucosa, placenta, prostate, dental and bone tissues, as well as submandibular epithelium (Rougeot, C. et al, *American Journal of Physiology*, (1997) 273, R1309–20; Sales et al., (1991) *Regulatory Peptides* 33, 209–22) and reviewed by Kenny et al., (1987), *Mammalian ectoenzymes* 169–210. There is evidence that, almost all these tissues contain substance P released from peripheral parasympathetic and sensory nerve terminals acting near the site of release on target cells that contain the neurokinin receptors to modulate the particular tissue function (McCarson et al., (1999), *Neuroscience* 93, 361–70). Thus, it appeared that the neuropeptide could be regarded as a relevant biologically NEP substrate at the periphery. However, substance P is cleaved potently by NEP and ACE membrane-bound peptidases, and both enzymes are highly distributed in the renal epithelium (Skidgel et al., (1985), *Progress in Clinical &Biological Research* 192, 371–8).

The specificity of the peptidase assay was assessed by testing the inhibitory efficacy of selective peptidase inhibitors (at 1–10 µM final concentration to induce maximum inhibitory response) on the endoproteolysis of 3H substance P by the various tissue-membrane enzymes, and by analysing the selective formation of the NEP-related tritiated product of the reaction that was defined, as above using spinal tissue. In addition, under standard conditions of initial velocity measurement, bestatin (10 µM) was added in the incubation medium to prevent unselectively the membrane aminopeptidase activities.

Figure 4A:
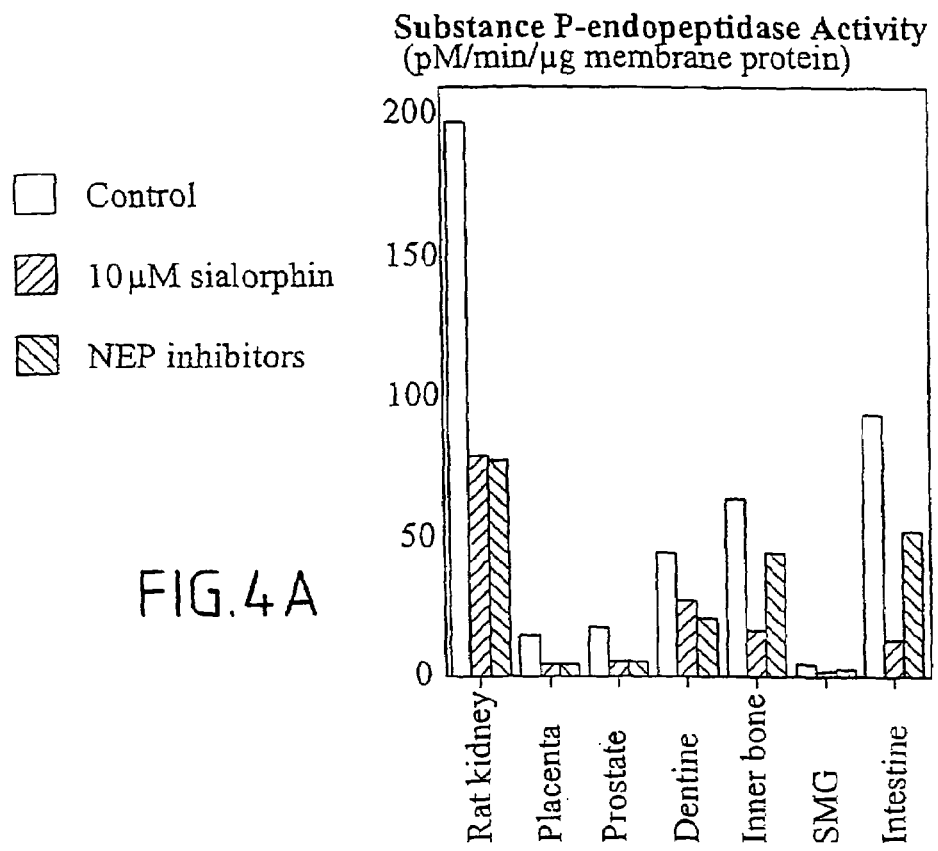
FIGS. 4 A and B: Substance P-catalytic activity of various peripheral rat tissue membranes and dose response inhibitory potency of SMR1-QHNPR (SEQ ID NO: 2) (sialorphin) on renal membranes.
Figure 4B:
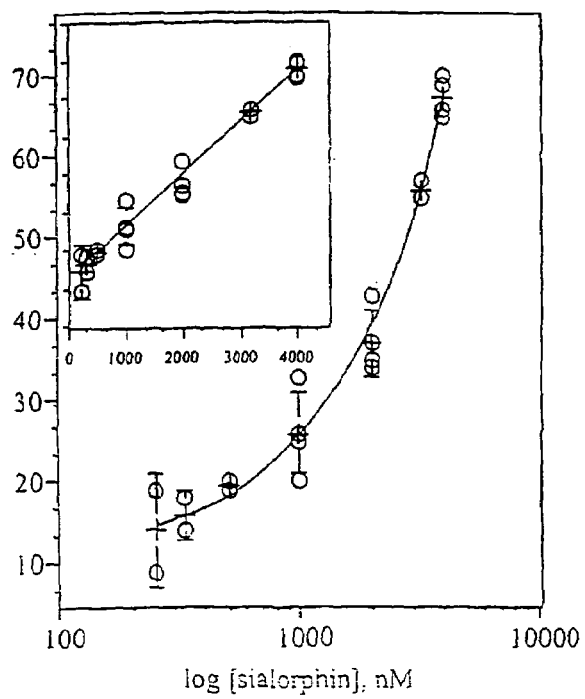

As shown in FIG. 4-A and in agreement with previous data, male rat kidney contained the highest level of substance-P-hydrolytic specific activity: 197 pM/min/µg membrane protein from which 61±10%, n=4 was due to NEP activity and 38±12% was the result of ACE activity. Sialorphin inhibited the renal membrane activity with equal effectiveness than the phosphoramidon NEP inhibitor, i.e., 60±5% of maximum inhibitory response (n=9). When inhibitory efficacy was tested on purified rabbit renal NEP by using substance P as substrate (Vi=140 pM/min/µg enzyme), it has been found that the substance P catabolism by the soluble-enzyme was already inhibited by sialorphin (46% for 5 µM).

Furthermore, the inhibitory effect of sialorphin on 3H substance-P degradation by rat kidney, shown in FIG. 4-B, was strictly dose-dependent (r=0.970, n=20) thus allowing to evaluate the inhibitory potency with IC50 values in the [0.5–1] micromolar range. This inhibitory potency is closely related to that obtained using purified rabbit renal NEP and synthetic specific fluorogenic substrate, i.e. 0.6 µM or using rat spinal NEP, i.e. 0.4 µM.

All these results indicated that the renal NEP/sialorphin molecular interaction that has been already evidenced after in vivo tissue uptake might lead to a physiological action, for instance protection of the NEP-induced metabolism of regulatory peptides present within this tissue, such as substance P, an humoral vasodilatory-proinflammatory mediator and autonomic neurotransmitter. Kidney that contains the highest NEP activity seems to be also a major site of ANP metabolism (Webb et al., (1989), *Journal of Cardiovascular Pharmacology* 14, 285–93). Thus, one can hypothesise that at renal sites sialorphin could also play a role in potentiating the physiological effects of this peptide messenger whose action is clearly regulated by NEP (Kenny et al. (1988) *FEBS Letters* 232, 1–8); ANP is a vasodilatory and natriuretic factor mediating physiological regulation of blood pressure, body fluid circulation and mineral homeostasis.

In rat placenta and prostate tissues, two other peripheral tissues richest in NEP, the levels of substanceP-endoproteolytic activity was 12–14-fold lower than in kidney and 74±10%, n=5 was shown to be due to NEP while only 8% was the result of ACE. Moreover, sialorphin decreased substance P degradation from these tissues by 70±3%. Prostate tissue was not seen to be accessible to a systemically administered hydrophilic compound such as sialorphin 3H-peptide, however this tissue is already able to synthesise it, suggesting a potential important local role for sialorphin, as inhibitor of endogenous peptidergic signal inactivation, such as substance P (Rougeot et al., (1994), *European Journal of Biochemistry* 219, 765–73; Rougeot, C. et al. (1997), *American Journal of Physiology* 273, R1309–20).

The most striking result comes from the observation that the rat inner dental tissue which is one of major targets for sialorphin, in vivo, showed high levels of substance-P endoproteolytic activity, i.e. 44 pM/min/µg membrane protein (Rougeot, C. et al. (1997), *American Journal of Physiology* 273, R1309–20. The addition of NEP inhibitors reduced 3H-substance P catabolic process by 53±4%, while ACE inhibitor reduced it by 21% and the sialorphin by 39±14%, n=4. In line with this result, is the present demonstration of sialorphin inhibitory efficacy by 75±10%, n=4 on the ectopeptidase-sensitive substance P degradation by inner bone tissues. The possible involvement of sialorphin in NEP function within these tissues is supported by the observation that the enzyme's localisation and activity in rat peripheral tissues well coincide with the tissue distribution and the density of sequestration sites for sialorphin; and these tissues included the skeletal and alveolar bones and the periosteal surfaces (Rougeot, C. et al. (1997), *American Journal of Physiology* 273, R1309–20; Sales et al., (1991), *Regulatory Peptides* 33, 209–22; Llorens et al., (1981), *European Journal of Pharmacology* 69, 113–6). Furthermore, from the inner bone and dental membrane extracts the major sialorphin-associated molecule exhibit a pI of 5.2±0.4, (n=5) and 5.7±0.6, (n=3), respectively, thus well correlating to the pI for NEP (5.5). However the physiological NEP-sensitive effector peptide(s) implicated in the regulation of skeletal and dental mineralisation and/or resorption processes remain to be identified.

A similar situation occurs for other structures previously demonstrated to be labelled by NEP-inhibitor or sialorphin such as the rat SMG (Rougeot, C. et al. (1997), *American Journal of Physiology* 273, R1309–20; Sales et al., (1991), *Regulatory Peptides* 33, 209–22). Indeed, the SMG level of substance-P-hydrolytic specific activity was found to be 4.2 pM/min/µg membrane protein and 55±12%, n=4 was due to NEP activity and 20% to ACE activity, whereas the addition of sialorphin resulted in 79% inhibition. This gland is the major site of sialorphin synthesis where it might be thus involved in the regulation of local protein and/or fluid secretions through modulation of activity of substance P, an extremely potent sialolog compound in rat (Yu et al., (1983), *Experimental Biology &Medicine* 173, 467–70).

Moreover some other richly supplied area is the gut, especially the intestinal wall which expresses NEP, contains substance P extrinsic sensory and enteric neurons and sialorphin uptake sites (Rougeot, C. et al. (1997), *American Journal of Physiology* 273, R1309–20; Holzer et al., (1997), *Pharmacology & Therapeutics* 73, 219–63). The substance-P endoproteolysis by membrane fractions of the rat intestine was found to be 93.5 pM/min/µg membrane protein. The inhibition profile showed that in the presence of NEP inhibitors 51% of the exogenous 3H substance P was saved from catabolic process, whereas addition of sialorphin induced powerful inhibitory response with 87±17%, n=3 protection.

Taken together, these results strongly indicate that in vitro the sialorphin efficiently prevents the endopeptidase-induced degradation of the neuropeptide or humoral mediator, substance P, which is available locally in a number of tissues where NEP and sialorphin synthesis and/or uptake are also located. This suggests that the circulating sialorphin contribute in vivo to the regulation of peripheral vasodilatory and proinflammatory actions of substance P. Furthermore, as a number of peripheral effects of circulating ANP are under NEP regulation, One can hypothesise that sialorphin also modulates its vasorelaxant, diuretic and natriuretic actions, especially at renal, intestine, bone and submandibular sites (Kenny et al., (1988), *FEBS Letters* 232, 1–8; Vargas et al., (1989), *Endocrinology* 125, 2527–31; Gonzalez et al., (2000), *Peptides* 21, 875–87).

Example 3

Sialorphin has Kinetic Behavioural Characteristics of a Competitive Inhibitor

In order to determine inhibitor modality, all the measures of initial velocity of the renal enzymatic reaction were plotted versus substrate concentration for several fixed inhibitor concentrations or versus inhibitor concentration for fixed substrate concentrations.

The pattern of lines in the untransformed (FIG. 5-A) and double-reciprocal plot (FIG. 5-B) as well as Dixon plot (FIG. 5-C) analyses of the inhibition by sialorphin on [3H] substance P catabolism by renal membrane are the characteristic signature of a competitive inhibition. Competitive inhibitors function through binding at the enzyme active site, hence competing directly with the substrate for the active free enzyme. Hence, the competition between sialorphin and substance P has the kinetic effect of raising the apparent Km of the enzyme for substrate by 2–5 fold.

Otherwise, tissue-uptake of the sialorphin peptide involves a complex molecular species, including a cation mineral element, as the peptide was only recovered in the presence of a strong divalent metal ion chelating agent (Rougeot, C. et al. (1997), *American Journal of Physiology* 273, R1309–20). Furthermore chelating-FPLC analyses showed that the sialorphin has a selective and strong zinc-chelating group, likely involving its histidine residue. The zinc ion, an essential component of the NEP catalytic site, is a common target of synthetic potent NEP inhibitors described elsewhere. Indeed, they were designed with a phosphate (phosphoramidon) or thiol (thiorphan) or hydroxamate groups (kelatorphan) as zinc-coordinating moiety, fitting the active site of metallopeptidase (reviewed by Roques et al., (1993), *Pharmacological Reviews* 45, 87–146).

Taking the kinetic behaviour of sialorphin into account in addition to the fact that the in vivo peptide interaction with its membrane receptor sites involved multivalent mineral ion, one can postulate that the sialorphin shares some structural communality with the transition state of the reaction, thus allowing to optimise interactions with groups in the enzyme active site, for instance as a zinc coordinating ligand.

The crystal structure determination of NEP when complexed with sialorphin would allow one to gain insight into the distinctive binding mode of this natural competitive inhibitor.

Example 4

Sialorphin, a New Class of Natural Analgesic

NEP plays a pivotal role in the control of biological activity of the neuropeptide signals involved in conveying sensory information of different modalities from the peripheral tissues (cutaneous, muscular and visceral areas) to multiple central and peripheral nervous system neuronal circuits. Prominent among these mediators is substance P, a sensory neurotransmitter and enkephalins, the analgesic neuromodulators (Dickenson, (1995), *British Journal of Anaesthesia* 75, 193–200). It is demonstrated here below that sialorphin potently prevents their extracellular catabolism by rat spinal tissues, in vitro.

The importance of enkephalins in modulating nociceptive information has been evidenced in pre-proenkephalin gene-deficient mice, which exhibited significant decrease in nociceptive thresholds (Konig, M. et al. (1996) *Nature* 383, 535–8). Conversely, using inhibitors of membrane-bound zinc metallopeptidases, NEP and APN which are both involved in the rapid inactivation of the enkephalins, resulted in potent analgesic responses (Chen et al., (1998) *Proceedings of the National Academy of Sciences of the United States of America* 95, 12028–33).

To extend the insight into the in vivo possible antinociceptive property of sialorphin through enkephalin-degrading enzyme inhibition, its effects were assessed in rat model of pain, i.e. the pin pain test, (Hebert et al. (1999) *Physiology & Behavior* 67, 99–105) in which the various behavioural parameters of pain responses were recorded with a 3-min cutoff time.

The in vivo activity of sialorphin was tested on the pin pain assay using male rats (350–400 g, Charles Rivers). The experimental device consists in an open-field (45×45×40 cm) which is divided into nine equal squares (150×150 mm), eight of them are peripheral and one is central. The peripheral squares are overlayed with stainless steel pins (2/cm2, length 8 mm and diameter 0.6 mm). The test consisted in placing the rat in the central square of the open-field and recording its different behaviours (cut-off time, 3 min). Two days before the pain test, the rats were familiarised with the experimental device without pins for 20 min, so as to reduce the stress linked to the spatial neophobia. All statistical analyses were carried out using the Statview 5 statistical package.

As shown in the FIG. 6-A, intravenous-administered sialorphin-treated rats emitted less vocalisation compared to vehicle-controls and displayed locomotor and exploratory activities in the peripheral pin-areas. For instance, 100 μg per kg body weight sialorphin produced profound analgesic response, as it induced significant increase in the frequency of crossings peripheral squares during the course of 3-min trial: 11.13±1.43, n=8 versus control 2.88±0.44, n=8, $p \leq 0.001$ by ANOVA and unpaired t-tests, as well as of rearings on peripheral squares: 3.88±0.83 versus 0.75±0.41, $p \leq 0.005$. In parallel, it induced significant decrease in the number of audible vocalisation—(0.25±0.16 versus 7.25±3.13 $p \leq 0.05$) and escape—(0.13±0.13 versus 6.88±2.47, $p \leq 0.05$) responses to painful stimuli.

Hence, sialorphin-treated rats displayed powerful morphine-like levels of analgesia, i.e., 74–97% analgesia at 100 μg/kg given intravenously, in the pin pain tests, in rat.

Furthermore, in a second test trial, the sialorphin-effect on these behavioural parameters of noxious response, showed in FIG. 6-B, were reversed by 42–63% by prior administration of 0.3 mg per kg body weight naloxone (subcutaneous-injection) a μ-opioid receptor antagonist (vocalisation parameter was 20% naloxone-reversible). In addition, as shown in FIG. 6-C, sialorphin-treated rats spent significantly less time in the central area of the open-field that is not pin-overlayed than controls (57.75±21.30 sec versus 155.13±14.21 sec, p=0.0019), and this behaviour was 56% nalaxone-reversible (112.38±17.44 sec). This demonstrates that μ-opiate receptor is required for complete pharmacological sialorphin-induced analgesic effect, thus supporting endogenous opioidergic mediation of sialorphin-induced analgesia. Mu-receptor dependent opioidergic pathways have an essential role in spinal and supraspinal control of nociceptive inputs and in morphine-induced analgesia (Besse et al., (1990) *Brain Research* 521, 15–22; Matthes et al., (1996), *Nature* 383, 819–23; Sora, I. et al., (1997) *Proceedings of the National Academy of Sciences of the United States of America* 94, 1544–9). Thus sialorphin might produce a part of its analgesic effects through potentiation of endogenous μ opioid-dependent pathways resulting to spinal and brain antinociception.

Example 5

Study of the Activity of the QHNPR (SEQ ID NO: 2) Peptide in the Aversive Light Stimulus Avoidance Test 1—Materials and Methods 1.1—Animals Twenty four male SPF Wistar/AF rats weighing from 300 to 320 g were used. Upon reception, the rats were weighed, marked and distributed, in groups of 3, into F-type polycarbonate cages. The animals were housed in an air-conditioned animal house at a temperature of 22–24° C. Food and drink was available to the rats ad libitum. They were subjected to a 12-hour light/dark cycle (light from 8 pm to 8 am).

After a period of familiarization with the laboratory conditions of one week, the 24 rats were randomly divided into 2 groups (n=12). The rats from the various groups were all handled in the same way and under the same conditions.

1.2—Materials

Device for Aversive Light Stimulus Avoidance Conditioning (ALSAT)

The experimental device consists of an isolated cage (50×40×37 cm) which is brightly lit and comprises two levers: one lever is active, making it possible, when it is operated, to obtain 30 seconds of darkness, followed by the return of the light, whereas the other lever is inactive (not positively reinforced). Pressing the active lever during the period of darkness does not produce further periods of darkness. The rat is placed in the cage for 20 minutes and the number of times each lever is pressed is counted during the experiment.

The test battery, composed of 4 conditioning devices, is entirely automated and computer-controlled. Thus, no experimenter is present in the room during the test.

1.3—Experimental Procedure

This model uses the aversion of the rat to a brightly lit environment. During the familiarization session and the learning session, the rat learns to control the aversive light environment of the test device in the context of operant conditioning: the animal learns to press the active lever in order to obtain periods of darkness.

The learning test is made up over two sessions:

Session 1, familiarization with the experimental device (day 1);

Session 2, learning test (day 2).

Variables Recorded

The number of times the active lever (AL) is pressed;

The number of times the inactive lever (IL) is pressed.

1.4—Products

| | Products | | | |
|---|---|---|---|---|
| | Product | | | |
| | QHNPR peptide | 0.01 N acetic acid | PBS | Distilled water |
| Origin | BACHEM Switzerland | Riedel de Haën Germany | Fluka Switzerland | Chaix and Du Marais France |
| Preparation method | Dissolved in acetic acid diluted in distilled water, and buffered with D-PBS | Diluted in distilled water | | |

1.5—Administration of Products

The QHNPR (SEQ ID NO: 2) peptide is suspended in a proportion of 500 μg per 5 ml of 0.01N acetic acid, and then diluted with PBS in order to be administered at the dose of 50 μg/kg, via the i.v. route, in the dorsal caudal vein of the rat, 1 minute before the test.

Product administration protocol

| Group | Rats per group | Treatment | Dose (μg/kg) | Route | Volume ml/kg | Administration before the test (minutes) |
|---|---|---|---|---|---|---|
| Vehicle | 12 | Acetic acid + PBS | — | I.V. | 0.7 | 1 |
| Peptide | 12 | FG6-005 | 50 | I.V. | 0.7 | 1 |

1.6—Statistical Analyses

A two-sided probability unpaired t-test was used to compare the lever-pressing activity of the two groups of rats.

In order to evaluate the distinction between the two levers, a two-sided probability paired t-test was used to compare the number of times the active lever was pressed with the number of times the inactive lever was pressed, within each of the groups.

The results are expressed as mean±standard error of the mean (SEM).

2—Results 2.1—Total Number of Times the Two Levers were Pressed During the Test Sessions During the two test sessions, the rats treated with the QHNPR (SEQ ID NO: 2) peptide proved to be significantly less active than the control rats in the aversive light stimulus avoidance test.

Total number of times the two levers were pressed during the test sessions

| | (mean ± SEM) | | |
|---|---|---|---|
| | Treatment | | |
| | Vehicle I.V. (n = 10) | Peptide 50 μg/kg, I.V. (n = 10) | Unpaired t-test (two-sided prob.) |
| Session 1 | 25.58 ± 6.15 | 10.08 ± 1.98 | t = 2.40; p < 0.05 |
| Session 2 | 21.50 ± 5.09 | 5.25 ± 5.09 | t = 3.08; p < 0.01 |

2.2—Distinction Between the Levers

During the two test sessions, the control rats press the active lever significantly more than the inactive lever.

This is not the case with the rats treated with the QHNPR (SEQ ID NO: 2) peptide, which make no distinction between the two levers.

Distinction between the levers during the test sessions

| | (mean ± SEM) | |
|---|---|---|
| | Treatment | |
| | Vehicle I.V. (n = 10) | Peptide 50 μg/kg, I.V. (n = 10) |
| Session 1 | | |
| Number of times AL pressed | 14.17 ± 3.52 | 4.83 ± 1.02 |
| Number of times IL pressed | 11.42 ± 2.68 | 5.25 ± 1.14 |
| Paired t-test (two-sided prob.) AL vs IL | t = 2.30; p < 0.05 | T = 0.49; N.S. |
| Session 2 | | |
| Number of times AL pressed | 12.83 ± 3.22 | 2.67 ± 0.47 |
| Number of times IL pressed | 8.67 ± 1.97 | 2.58 ± 0.94 |
| Paired t-test (two-sided prob.) AL vs IL | t = 2.63; p < 0.05 | T = 0.13; N.S. |

AL: active lever;
IL: inactive lever.

3—CONCLUSION

Under these experimental conditions, during the two test sessions, the rats treated with the QHNPR (SEQ ID NO: 2) peptide prove to be significantly less active than the control rats in the aversive light stimulus avoidance test. Furthermore, they show no learning, since they make no distinction between the two levers.

Either these rats are less sensitive to the nociceptive light stimulus, or they are more sensitive to the stress of the experimental light environment. Given that it has been directly observed that these rats have satisfactory locomotor and exploratory activity during the tests, it is the fact that they are less sensitive to the aversive stimulus which explains their performance. The peptide thus exhibits analgesic activity.

The control rats show satisfactory activity with regard to manipulating the levers and make a distinction between the active lever and the inactive lever, both during the first session and during the second session.

The invention claimed is:

1. A method for treating or reducing the severity of a disease or disorder mediated by a membrane metalloproteinase comprising:
   administering to a subject in need thereof an amount of a SMR-1 (submandibular rat 1 protein) peptide sufficient to modulate the activity of a metalloproteinase,
   wherein the SMR1-peptide comprises a sequence shown by formula (1):

$X_1QHX_2X_3X_4$ (SEQ ID NO: 11)

wherein
   $X_1$ is absent from formula (1) or is selected from the group consisting of R, G, RR, PRR, GPRR, RGPRR and VRGPRR,
   $X_2$ is N, G or D,
   $X_3$ is P or L and
   $X_4$ is R or T.

2. The method of claim 1, wherein said metalloproteinase is a membrane-zinc metallopeptidase.

3. The method of claim 1, wherein an amount of said SMR-1 peptide sufficient to modulate NEP (neutral endopeptidase)-induced degradation of an NEP sensitive peptide is administered to a mammal.

4. The method of claim 3, wherein said amount of SMR-1 peptide is sufficient to inhibit NEP.

5. The method of claim 3, wherein said amount of SMR-1 peptide is sufficient to inhibit enkephalin degradation.

6. The method of claim 1, wherein said amount of SMR-1 peptide is sufficient to provide an antinociceptive effect.

7. The method of claim 1, wherein said amount of SMR-1 peptide is sufficient to provide analgesia.

8. The method of claim 1, wherein said disease or disorder is characterized by chronic inflammatory pain.

9. The method of claim 8, wherein said disease or disorder is arthritis or inflammatory bowel disease.

10. The method of claim 1, wherein said disease or disorder is diarrhea.

11. The method of claim 1, wherein said amount of the SMR-1 peptide is sufficient to inhibit endogenous A II formation and inhibit inactivation of substance P, BK (bradykinin) and/or ANP (atrial natriuretic peptide).

12. The method of claim 1, wherein said disease or disorder is hypertension.

13. The method of claim 1, wherein said amount of SMR-1 peptide is sufficient to exert natriuretic activity.

14. The method of claim 1, wherein said amount of SMR-1 peptide is sufficient to exert a diuretic activity.

15. The method of claim 1, wherein said disease or disorder is atherosclerosis.

16. The method of claim 1, wherein said disease or disorder is characterized by malignant cell proliferation and/or dissemination.

17. The method of claim 1, wherein said disease or disorder is a viral or bacterial infection.

18. The method of claim 1, wherein said disease or disorder is characterized by an abnormal immuno-inflammatory response.

19. The method of claim 1, wherein said disease or disorder is drug abuse.

20. The method of claim 1, wherein the SMR1-peptide is the SMR1 protein, or a maturation product of the SMR1 protein.

21. The method of claim 1, wherein the SMR1-peptide comprises one or more amino acids in the D-form.

22. The method of claim 1, wherein the SMR1-peptide further comprises a group for enhancing bioavailability or enhancing resistance to enzymatic degradation.

23. The method of claim 1, wherein the SMR1-peptide is associated with a second pharmaceutical agent that acts synergistically with the SMR1-peptide.

24. The method of claim 1, wherein $X_1$ is absent from formula (I).

25. The method of claim 1, wherein $X_1$ is R or G.

26. The method of claim 1, wherein $X_1$ is RR, PRR, or GPRR.

27. The method of claim 1, wherein $X_1$ is RGPRR or VRGPRR.

28. The method of claim 1, wherein $X_2$ is N.

29. The method of claim 1, wherein $X_2$ is G.

30. The method of claim 1, wherein $X_2$ is D.

31. The method of claim 1, wherein $X_3$ is P.

32. The method of claim 1, wherein $X_3$ is L.

33. The method of claim 1, wherein $X_4$ is R.

34. The method of claim 1, wherein $X_4$ is T.

35. A method for treating or reducing the severity of a disease or disorder mediated by a membrane metalloproteinase comprising:
   administering to a subject in need thereof an amount of a modified SMR-1 (submandibular rat 1 protein) peptide sufficient to modulate the activity of a metalloproteinase,
   wherein the modified SMR1-peptide comprises a sequence shown by formula (1):
   $X_1QHX_2X_3X_4$ (SEQ ID NO: 11),
   wherein
   $X_1$ is absent from formula (1) or is selected from the group consisting of R, G, RR, PRR, GPRR, RGPRR and VRGPRR, $X_2$ is N, G or D,
$X_3$ is P or L and
$X_4$ is R or T;
wherein said modification is at least one selected from the group consisting of incorporating of one or more D-amino acids into the SMR1 peptide sequence, protecting one or more amino acid side chains with a protecting group, protecting one or more $NH_2$ or COOH functions in the SMR1 peptide, replacing of one or more amide bonds in the SMR1 peptide with a non-amide bond, introducing one or more double bonds into the SMR1 peptide sequence, introducing retroinversion or reduction isomers of the CO—NH amide bonds, methylation of at least one amide function in the SMR1 peptide, modifying the SMR1 peptide to have more than one N or C terminus, introducing one or more conformational restraints into the SMR1 peptide, cyclizing the SMR1 peptide, introducing stereospecificity into the SMR1 peptide, and dimerizing the SMR peptide.

* * * * *

SEQUENCE LISTING

<160> NUMBER OF SEQ ID NOS: 8

<210> SEQ ID NO 1
<211> LENGTH: 5
<212> TYPE: PRT
<213> ORGANISM: Rattus rattus
<220> FEATURE:
<221> NAME/KEY: MISC_FEATURE
<222> LOCATION: (1)..(1)
<223> OTHER INFORMATION: X is selected from any one amino acid

<400> SEQUENCE: 1

Xaa His Asn Pro Arg
1               5

<210> SEQ ID NO 2
<211> LENGTH: 5
<212> TYPE: PRT
<213> ORGANISM: Rattus rattus

<400> SEQUENCE: 2

Gln His Asn Pro Arg
1               5

<210> SEQ ID NO 3
<211> LENGTH: 6
<212> TYPE: PRT
<213> ORGANISM: Rattus norvegicus

<400> SEQUENCE: 3

Arg Gln His Asn Pro Arg
1               5

<210> SEQ ID NO 4
<211> LENGTH: 11
<212> TYPE: PRT
<213> ORGANISM: Rattus norvegicus

<400> SEQUENCE: 4

Val Arg Gly Pro Arg Arg Gln His Asn Pro Arg
1               5                   10

<210> SEQ ID NO 5
<211> LENGTH: 5
<212> TYPE: PRT
<213> ORGANISM: Rattus rattus

<400> SEQUENCE: 5

Gln His Asn Leu Arg
1               5

<210> SEQ ID NO 6
<211> LENGTH: 6
<212> TYPE: PRT
<213> ORGANISM: Rattus rattus

<400> SEQUENCE: 6

Arg Gln His Asn Leu Arg
1               5

<210> SEQ ID NO 7
<211> LENGTH: 6
<212> TYPE: PRT
<213> ORGANISM: Mus musculus

```
-continued

<400> SEQUENCE: 7

Gly Gln His Gly Pro Arg
1               5

<210> SEQ ID NO 8
<211> LENGTH: 6
<212> TYPE: PRT
<213> ORGANISM: Mus musculus

<400> SEQUENCE: 8

Gly Gln His Asp Pro Thr
1               5
```